United States Patent
Ward et al.

(10) Patent No.: US 10,362,783 B2
(45) Date of Patent: *Jul. 30, 2019

(54) SOLUTIONS EMPLOYING HERBICIDES AND BUFFERED AMINE OXIDES TO KILL WEEDS AND RELATED METHODS

(71) Applicant: KOP-COAT, INC., Pittsburgh, PA (US)

(72) Inventors: Hans A. Ward, Wexford, PA (US); Ronald Walton Clawson, Jr., Monroeville, PA (US); Kenneth Allen Cutler, Verona, PA (US); Cameron R. Scott, Rotorua (NZ)

(73) Assignee: KOP-COAT, INC., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/238,916

(22) Filed: Aug. 17, 2016

(65) Prior Publication Data

US 2016/0353741 A1    Dec. 8, 2016

Related U.S. Application Data

(62) Division of application No. 14/674,498, filed on Mar. 31, 2015.

(51) Int. Cl.
| | | |
|---|---|---|
| *A01N 57/20* | (2006.01) | |
| *A01N 37/38* | (2006.01) | |
| *A01N 43/40* | (2006.01) | |
| *A01N 43/50* | (2006.01) | |
| *A01N 37/10* | (2006.01) | |
| *A01N 25/30* | (2006.01) | |

(52) U.S. Cl.
CPC ........... *A01N 57/20* (2013.01); *A01N 25/30* (2013.01); *A01N 37/10* (2013.01); *A01N 37/38* (2013.01); *A01N 43/40* (2013.01); *A01N 43/50* (2013.01)

(58) Field of Classification Search
CPC ......... A01N 37/10; A01N 43/40; A01N 57/20
USPC .......................................................... 514/206
See application file for complete search history.

(56) References Cited

U.S. PATENT DOCUMENTS

| | | | |
|---|---|---|---|
| 4,093,442 A | 7/1978 | Schmidt et al. | |
| 5,710,103 A * | 1/1998 | Magin | A01N 57/20 504/206 |
| 5,833,741 A | 11/1998 | Walker | |
| 5,846,305 A | 12/1998 | Payzant | |
| 6,274,199 B1 | 8/2001 | Preston et al. | |
| 6,340,384 B1 | 1/2002 | Walker | |
| 6,375,727 B1 | 4/2002 | Walker | |
| 6,416,789 B1 | 7/2002 | Marks et al. | |
| 6,448,279 B1 | 9/2002 | Tseng et al. | |
| 6,508,869 B2 | 1/2003 | Tseng et al. | |
| 6,527,981 B1 | 3/2003 | Tseng et al. | |
| 6,572,788 B2 | 6/2003 | Walker | |
| 6,811,731 B2 | 11/2004 | Archer et al. | |
| 7,056,919 B2 | 6/2006 | Ross et al. | |
| 7,655,281 B2 | 2/2010 | Ward et al. | |
| 7,896,960 B2 | 3/2011 | Ward et al. | |
| 2002/0065206 A1 | 5/2002 | Tseng et al. | |
| 2005/0008576 A1 | 1/2005 | Makansi | |
| 2009/0062127 A1 | 3/2009 | Liu | |
| 2009/0088481 A1 | 4/2009 | Ward et al. | |
| 2012/0258248 A1 * | 10/2012 | Ross | B27K 3/0285 427/337 |
| 2013/0172184 A1 | 7/2013 | Bain et al. | |
| 2014/0235445 A1 | 8/2014 | Sanders | |

FOREIGN PATENT DOCUMENTS

| | | |
|---|---|---|
| EP | 2473035 A2 | 7/2012 |
| EP | 1273234 A1 | 1/2013 |
| EP | 2615921 A1 | 7/2013 |
| WO | WO2013189777 A1 | 12/2013 |
| WO | WO2014191096 A1 | 12/2014 |

OTHER PUBLICATIONS

Andrew D. Malec, et al., Improving Water Soluble Agricultural Formulations With Amine Oxides, proc. ISAA 2013, pp. 85-89.
Label for Warrior © Dandelion and Week Killer Concentrate.
Label for Roundup ® Weed and Grass Killer Concentrate.

* cited by examiner

Primary Examiner — Johann R Richter
Assistant Examiner — Courtney A Brown
(74) Attorney, Agent, or Firm — Eckert Seamans Cherin & Mellott, LLC; Arnold B. Silverman

(57) ABSTRACT

Solutions for killing weeds include a herbicide admixed with a buffered amine oxide. The synergism between the two components reduces the amount of herbicide which must be employed to achieve an effective weed kill. Related methods involve application of the solution to the weeds to be killed.

63 Claims, No Drawings

SOLUTIONS EMPLOYING HERBICIDES AND BUFFERED AMINE OXIDES TO KILL WEEDS AND RELATED METHODS

BACKGROUND OF THE INVENTION

1. Field of the Invention

The present invention relates to improved solutions for killing weeds by employing herbicides in combination with buffered amine oxides and to methods employing such solutions.

2. Description of the Prior Art

The problem of weeds has long existed in many environments including, but not limited to agriculture, parks, golf courses, residential environments, highways, vegetable gardens, floral gardens, railroad tracks, recreational facilities, forests, pastures, waterways and in many other environments. Weeds can interfere with desired functionality, the health of adjacent plants, as well as the aesthetics of an area containing vegetation.

Weeds also can present numerous health problems for people and animals. Weeds can also have a role in affecting the quality of human life such as those afflicted with allergies, for example. Also, health problems can result from airborne pollen from plants, such as ragweed, or direct contact with plants such as poison ivy or poison oak or poison sumac, for example.

It has been known to employ various types of herbicides to kill weeds. Two very well-known herbicides are Glyphosates, which kills weeds and grass such as that sold under the trade designation Roundup, for example, and 2,4 Dichlorophenoxyacetic acid, also known as 2,4-D. which kills weeds, but not grass, such as that sold under the trade designation Weed Warrior, for example. Systemic herbicides have also been known.

Ward, U.S. Pat. No. 7,896,960 discloses a method and solution for providing enhanced penetration of wood preservatives into wood to a greater depth through synergism between a buffering agent and an amine oxide. It contemplates the use of various types of wood preservatives on wood after it has been severed from a living tree. Green lumber is also said to be treatable by the system.

U.S. Pat. No. 6,811,731 is directed toward a fire-retardant wood-based composite created by treating a green wood furnish with a phosphate/borate fire-retardant material. The fire-retardant treated green wood furnish is blended with a binder and then bound by applying pressure to form a non-leaching fire retardant wood based composite.

European patent publication EP 2615921 discloses an amine and amine oxide surfactants for controlling sprayed herbicide so as to avoid undesired drift of the sprayed material. This is said to be accomplished by controlling the droplet size, as smaller droplets are said to have a higher propensity for off-target movement. Undesired drift is said to cause damage to plants in a manner not desired.

Walker, U.S. Pat. No. 6,572,788 discloses the use of amine oxides as wood preservatives. It states that the amine oxides inhibit microbial growth in wood. This patent relates to wood which has been severed from growing trees and discloses the use of wood preservatives which are said to inhibit destructive organisms such as fungi and sapstain, for example. This disclosure is not directed toward destroying living weeds but, rather, the focus is on preserving structural integrity of wood after the tree has been killed and resisting destruction of the resultant lumber as the prime objective.

Tseng, U.S. Pat. No. 6,508,869 discloses the use of amine oxides to enhance the performance of boron compounds as wood preservatives. There is mention of the amine oxides improving the effectiveness of boron compounds as insecticides or biocides and plant growth regulating agents. They are also said to provide better dispersion of boron compounds when applied to plants and fungi. It also makes reference to the seeds of plants and the area on which the plants or fungi grow. There is no disclosure directed toward killing of weeds or other plants.

There remains, therefore, a very real and substantial need for an improved system for more economically achieving the objectives of (a) destroying weeds or (b) destroying weeds and grass while resisting damage to or destruction of desired plants.

SUMMARY OF THE INVENTION

Depending upon whether the objective is to kill weeds, but not grass, or weeds and grass, a herbicide suitable for that purpose is selected and combined with the buffered amine oxide to create the solution with the concentration of the combined herbicide and buffered amine oxide appropriate for the targeted plant or plants to be killed.

In a preferred practice of the invention, a buffered amine oxide system is employed as an additive to herbicidal formulations in order to enhance the performance of the herbicides on weeds. This enhancement resulted in a larger amount of weed kill while using less herbicide than otherwise would be required to effect a lesser or the same level of weed kill.

It is an object of the present invention to provide a method and related solution for using a sprayable composition of a herbicide and a buffered amine oxide formulation to destroy weeds or destroy weeds and grasses.

It is a further object of the invention to provide an efficient and economical solution and method of application employable in the destruction of weeds or weeds and grasses, which can employ conventional means of distribution of the solution on the targeted plants.

It is a further object of the present invention to destroy undesired and uncontrolled weeds which can have a significant negative impact on production of agricultural products and the health of a wide variety of other desired plants.

It is a further object of present invention to provide such a system which, through selection of the herbicide, will result in destruction of weeds, while not destroying adjacent plant life such as, for example, desired grasses.

It is a further object of the present invention to enhance the performance of herbicides to create a higher degree of weed kill using less herbicide.

It is an object of the present invention to provide a solution and related method which enhances the performance of herbicides by combining them with buffered amine oxides to produce a synergistic effect.

It is an object of the present invention to provide such a system which will permit visual determination that the desired kill has been accomplished without requiring special inspection equipment or testing.

It is yet another object of the present invention to provide solutions employing herbicides and buffered amine oxides to kill weeds and related methods wherein admixed with said solutions and employed in such methods are insecticides, fungicides or both to preserve living plants which may receive some of the solution during use of the methods of the present invention.

These and other objects of the invention will be fully understood from the following description of the invention.

DESCRIPTION OF THE PREFERRED EMBODIMENTS

As employed herein, the term "weed" or "weeds" means a living plant in any part of its life cycle which is growing where it is not wanted, and is sought to be killed through use of the present invention. The term "weed" has only limited botanical significance as a plant may be a weed in one context, but not another such as dandelions growing in the middle of a lawn, as opposed to dandelions being grown for use in salads, for example. Another example would be a plant such as honeysuckle, kudzu or certain grasses which might be desirable within certain confines but, due to aggressive reproduction or invasiveness outside of its original location, becomes a plant which is, to that extent, undesirable and, therefore, would be considered a weed. In addition to those weeds which were subject to testing reported herein in TABLES 1 through 14, among the plants frequently considered weeds are the following: Bermuda grass, bindweed, broad leaf plants, broadleaf plantain, woody plants, burdock, common lambsquarters, Virginia creeper, creeping Charlie, dandelion, goldenrod, Japanese knotweed, kudzu, leafy spurge, milk thistle, poison ivy, ragweed, fern,sorrel, striga, St. John's wort, sumac, radiata pine, tree of heaven, bamboo, which is a hollow grass, wild carrot, wood sorrel and yellow nutsedge, for example.

As employed herein, "kill" or "killed" means with respect to a weed, that the weed is dead and decayed.

As employed herein, the term "grass" or "grasses" means a plant of the family "true grasses" sedges and rushes, Graminoid (or Poaceae) characterized by mostly herbaceous, but sometimes woody plants with hollow and jointed stems, narrow sheathing leaves, petalles flowers borne in spikelets and fruit in the form of seed-like grain. Such plants are frequently employed collectively in lawns or employed as pasture for grazing animals or as ornamental plants or cut and dried as hay. This term shall also include, but not be limited to, bamboo, sugar cane, as well as cereal grains such as barley, corn, oats, rice, rye and wheat.

As employed herein, the term "2,4-D" means the herbicide having as an active ingredient 2,4-Dichlorophenoxyacetic acid and its salts and other types of related formulations.

The amine oxides may be mixed with buffers in a solvent, such as water, to create a buffered amine oxide solution and then mixed with a herbicide solution. The preferred amine oxides are selected from the group consisting of (a) the 12 carbon length amine oxides such as that sold under the trade designation Barlox 12 and (b) a mixture of the 12 and 18 carbon lengths sold under the trade designation Barlox 1218. The buffer system has the property that the pH of the solution changes very little when a small amount of a strong acid or strong base is added to it. Buffer solutions are employed as a means of keeping pH at a nearly constant value within a wide range of chemical operations. In the present invention, the buffer system helps to maintain a substantially constant pH when in contact with biological systems, such as living plants.

As employed herein, a "buffer system" is an aqueous solution consisting of a mixture of a weak acid and its conjugate base or a weak base with its conjugate acid. A buffer system may also be obtained by adding a weak acid/conjugate base or a weak base/conjugate acid or by adding the weak acid/weak base and a strong acid/strong base in sufficient amount to form the conjugate acid/conjugate base.

The buffer system concepts can be extended to polyprotic species in which one or more protons may be removed to form different buffer systems, i.e., phosphate systems. Among the preferred buffers are ammonium salt/ammonia, Deprotonated Lysine/Doubly Deprotonated Lysine, Potassium Phosphate Monobasic/Potassium Phosphate Dibasic, Potassium Bicarbonate/Potassium Carbonate, Boric Acid/Borax, Potassium Phosphate Dibasic/Potassium Phosphate Tribasic, Ammonium Citrate Tribasic, and Potassium Phosphate Monobasic/Potassium Phosphate Dibasic.

It will be appreciated that the buffered amine oxides do not significantly alter the pH of the herbicide products but, rather, make the pH much less likely to change based on the buffer capacity of the buffer additives.

A series of tests were performed in North America and in New Zealand to determine the effectiveness as week killers of a wide variety of herbicides and buffered amine oxide systems in different concentrations. The herbicides used in these tests were: 2, 4-Dichlorophenoxyacetic acid dimethylamine salt (herein "2,4-D") (which can be used alone or mixed with other chlorophenoxy types), glyphosate (glyphosate salts and other formulations of glyphosate), and a blend of picrolam and triclopyr.

EXAMPLE 1

A series of field trials were conducted in order to evaluate the effect of buffered amine oxide additives employed with herbicides for the killing of weeds. Concentrates of the buffered amine oxide and herbicide were diluted with water either in separate containers with subsequent combination thereof to create the solution or, in the alternative, the concentrates were placed in the same container with subsequent dilution with water.

Details regarding the field tests and results performed in North America are shown in TABLES 1 through 8. The results of field tests conducted in New Zealand are presented in TABLES 9 through 14.

The weeds chosen for testing in the respective geographic regions were selected because of their relative significance as a potentially troublesome plants in either North America or New Zealand with some consideration being given to the effectiveness of the two dominant commercial herbicides, i.e., 2,4-D and Glyphosate in combination with a number of buffered amine oxide systems in a number of concentrations. Also, economic aspects regarding the economic benefit of reducing the amount of herbicide required to achieve the same or a superior result was given consideration.

The following weeds were tested in the United States: raspberry, grass, multiflora rose and blackberry. The weeds tested in New Zealand were broom, fern, and gorse, blackberry and fesques.

TABLE 1

| Herbicide Type Product Concentration Dilution V/V | | Buffered Amine Oxide Formulation[8] Dilution | Weed Type and Kill[10] Rate (%) 1 Year After Application[5] | |
|---|---|---|---|---|
| 2,4-D[6] | Glyphosate[7] | V/V[9] | Raspberry | Grass[4] |
|  |  |  | 0[1][2] | 0[1][3] |
| 50:1 |  |  | 60) | — |
| 100:1 |  |  | 0 | — |
| 200:1 |  |  | 0 | — |
|  | 50:1 |  | — | 50) |
|  | 100:1 |  | — | 0 |
|  | 200:1 |  | — | 0 |
|  |  | 50:1 | 0 | 0 |
|  |  | 100:1 | 0 | 0 |
|  |  | 200:1 | 0 | 0 |
| 50:1 |  | 50:1 | 100 | — |
| 100:1 |  | 100:1 | 80 | — |
| 200:1 |  | 200:1 | 60 | — |
|  | 50:1 | 50:1 | — | 90 |
|  | 100:1 | 100:1 | — | 90 |
|  | 200:1 | 200:1 | — | 70 |

TABLE 1 shows the result of using the distilled water solutions on (a) 20 mature raspberry plants and (b) 10 plots of 90,000 square millimeters of grass plants. The grasses were of mixed types and included fesque grasses. Twenty milliliters per plant or plot was applied with low volume hand applied volumetric sprayer. The same quantity and mode of application were employed in the tests reported in TABLES 7 and 8.

The commercial herbicide mixture concentrate shown in column 1 contained:
- 4.55% Dimethylamine salt of 2,4-Dichlorophenoxyacetic acid, and
- 4.58% Dimethylamine salt of 2-(2-methyl-4-chlorophenoxy) propionic acid, and
- 4.53% Dimethylamine salt of 2-(2,4-Dichlorophenoxy) propionic acid The commercial herbicide concentrate shown in column 2 contained glyphosate which was 27% glyphosate isopropylamine salt.

The buffered amine oxide formula (column 3) based upon weight percent was 8.67% water, 14.00 ethylene glycol, 8.85 5 Mol Borax, 7.48% boric acid, 61.00 Barlox 12 (70% water and 30% amine oxide).

The control was distilled water without herbicide or buffered amine oxide.

In preparing the herbicide solutions the product label instructions were employed.

The field tests resulting in the data contained in TABLE 1 were performed during the period of Jun. 2, 2004 through Jun. 10, 2005. The plants were checked every three months after spraying.

Referring to TABLE 1, column 1 under the herbicide type is the 2,4-D herbicide and column 2 is glyphosate with each indicating several different concentrations. The buffered amine oxide system dilution volume to volume is stated in column 3. When the buffered amine formulation is combined with one of the two herbicides, the concentration listing refers to the total solution with the buffered amine oxide formulation added to the herbicide. Under the weed-type and kill rate in percentage, the first column refers to raspberry plants and the second to grass of mixed varieties. The examination occurred one year after application. This does not mean that it took that long to kill the plant when killing occurred which is much earlier but, rather, to verify that killing had, in fact, occurred.

Considering first the results of raspberry viewed one year after application, the 2,4-D in the concentration of 50:1 had a kill rate of 60%. The Glyphosate employed alone had 0 grass kills. The buffered amine oxide employed alone in the 100:1 and 200:1 2,4-D all had 0 kills of raspberry or grass. The combination of the 2,4-D with the buffered amine oxide each in a 50:1 concentration had a 100% kill rate, in a 100:1 concentration had a 80% kill rate and 200:1 had a 60% kill rate, thereby showing the synergistic action of the herbicide and buffered amine oxide to create a successful kill rate in a range of concentrations in respect of raspberry. This shows that in areas where it is desired to kill certain plants such as raspberry, this combination provides an effective choice. This combination was effective in the concentration ranges of about 50:1 through 200:1 with the preferred range being about 50:1 to 100:1.

Considering the Buffered Amine Oxide formulations in combination with Glyphosate each in concentrations of 50:1, 100:1 and 200:1, there were respectively 90%, 90% and 70% killing of grass.

It would appear that the combination of Glyphosate and buffered amine oxide each within the range of 50:1 through 200:1, would kill grass with the preferred range being about 50:1 to 100:1. It is well known that 2,4-D does not kill grass.

The test results of TABLE 1, therefore, shows that combinations of herbicide with buffered amine oxide formulation can be selected in such a way as to kill a plant considered to be a weed while not having any negative effect on the health of the grass or, in the alternative, killing a plant considered to be a weed while killing grass also.

The buffered amine oxide solution was added to the diluted herbicide solution on a volume to volume basis.

The same buffered amine oxide system employed in the tests reported in TABLE 1 were employed in connection with TABLE 2.

On Jun. 14 of 2005, further trials were conducted near Warren Pennsylvania, USA to evaluate the contribution of certain formulation components to herbicide performance from the Jun. 2, 2004 Buffered Amine Oxide system. The same field trial methods were used. The control was distilled water.

TABLE 2

| Herbicide Type Product Concentrate Dilution V/V | | Component Percent Weight of Buffered Amine Oxide Formula (Jun. 2, 2004)[8] | | | | Weed Type and Kill Rate[10] % 1 Year After Application[5] | |
|---|---|---|---|---|---|---|---|
| 2,4-D[6] | Glyphosate[7] | Ethylene Glycol | 5 Mol Borax | Boric Acid | Barlox 12 | Raspberry | Grass[4] |
|  |  |  |  |  |  | 0[(1)(2)] | 0[(1)(3)] |
| 50:1 |  |  |  |  |  | 50 |  |
| 200:1 |  |  |  |  |  | 0 |  |
|  |  | 0.07 |  |  |  | 0 | 0 |
|  |  |  | 0.044 |  |  | 0 | 0 |
|  |  |  |  | 0.037 |  | 0 | 0 |
|  |  |  |  |  | 0.305 | 0 | 0 |
| 200:1 |  | 0.07 |  |  |  | 0 |  |
| 200:1 |  | 0.07 | 0.044 |  |  | 0 |  |
| 200:1 |  | 0.07 | 0.044 | 0.037 |  | 0 |  |
| 200:1 |  | 0.07 | 0.044 | 0.037 | 0.305 | 70 |  |
|  | 50:1 |  |  |  |  |  | 50 |
|  | 200:1 |  |  |  |  |  | 0 |
|  | 200:1 | 0.07 |  |  |  |  | 0 |
|  | 200:1 | 0.07 | 0.044 |  |  |  | 0 |
|  | 200:1 | 0.07 | 0.044 | 0.037 |  |  | 0 |
|  | 200:1 | 0.07 | 0.044 | 0.037 | 0.305 |  | 70 |

The two herbicides which were tested were 2,4-D and Glyphosate. They were used in concentrations of 50:1 and 200:1. The vegetations tested were raspberry and grass. The components of the various elements employed in the buffered amine oxide formula are expressed in weight percent of the total buffered amine oxide formula. As seen in TABLE 2, Ethylene Glycol, 5 Mol Borax, Boric Acid and Barlox 12 which has 30% of 12 carbon length amine oxide, employed alone, failed to kill either the raspberry (weed) or grass. The first three components were tested at 200:1 strength with the Ethylene Glycol used alone, the Ethylene Glycol used in combination with 5 Mol Borax and Ethylene Glycol, 5 Mol Borax and Boric Acid used in combination. None of these killed the weeds. The combination of the four components and 2,4-D resulted in 70% killing of the weed (raspberry) as compared with the 50:1 2,4-D alone killing 50% of the raspberry and 200:1 alone having 0 kills of the raspberry.

Where a "0" appears in a block in TABLE 2, this means there were no kills. Where a block is blank, this means that no measurement was taken.

Referring to the Glyphosate, it, in a 50:1 concentration alone killed 50% of the grass. The 200:1 Glyphosate with the first three components shown in TABLE 2 under the amine oxide formula alone and in combination, had 0 kills of grass and the 200:1 Glyphosate alone had 0 kills of grass. The use of all four components resulted at 200:1 Glyphosate concentration resulted in 70% kill of grass.

In July of 2006, the final impact on long term weed kill tests confirmed the following:
1) Ethylene Glycol alone added no benefit to Herbicide performance.
2) 5 Mol Borax alone or in combination with Glycol added no benefit to Herbicide performance.
3) Boric Acid alone or in combination with Glycol added no benefit to Herbicide performance.
4) Barlox 12 (30% of 12 carbon length amine oxide) added no benefit alone or in combination with the other components individually.
5) The full four component Buffered Amine Oxide formula provided performance benefits to both Herbicides.

The data, therefore, show that the 2,4-D in a concentration of 200:1, had a 0 kill rate and in a concentration of 50:1 had a 50% kill rate of the raspberry and, in combination in a concentration of 200:1 with the other four constituents in the indicated quantities, had a kill rate of raspberry of 70%. Also, Glyphosate, in a concentration of 50:1 alone, had a 50% kill grass rate and the 200:1 concentration with the other four components, had a kill rate of 70%. See footnote 8 for TABLE 1 for buffered amine oxide formulation which was also used in TABLES 2 and 3.

On Jun. 5, 2007 an additional field trial was conducted near Warren, Pa., USA to evaluate increased concentrations of buffer components used in the Jun. 14, 2005 study in the Buffered Amine Oxide formula. The same field trial methods were used except no Ethylene Glycol was used and only Raspberry was tested with 2,4-D.

TABLE 3 shows additional testing of the herbicide 2,4-D with the same ingredients with 5 Mol Borax, Boric Acid and (Barlox 12) amine oxide in the amount and a weight basis of about 25% to 35% and preferably about 30%, but not Ethylene Glycol being employed and with the testing of the weed limited to raspberry. No testing with grass was performed. As was the case in TABLE 2, use of the herbicide 2,4-D in a 50:1 concentration produced a 50% kill rate one year after application. The use of 5 Mol Borax in combination with Barlox 12 produced a 40% kill rate. The use of 50:1, 2,4-D with Boric Acid and Barlox 12 in a 50:1 concentration produced a 50% kill rate. The use of 200:1, 2,4-D with all three components in a 200:1 concentration produced a 70% kill rate. Boric Acid, when used alone even in double the concentration as compared with the TABLE 2 reported experiments, did not produce any kills and even when mixed with Barlox 12, produced at a 50:1 2,4-D concentration, the same result as 2,4-D without these components. Also, the amine oxide employed alone with the herbicide produced no benefit.

In July 2008, the final impact on long term weed kill (TABLE 3) confirmed the following:
1) Boric Acid alone (even when doubled the amount reported in TABLE 2) provided no benefit to 2,4-D type Herbicide performance even when mixed with amine oxide.
2) 5 Mol Borax alone (even when doubled the amount reported in TABLE 2), provided no benefit to 2,4-D type Herbicide performance even when mixed with amine oxide.
3) Amine oxide alone and with herbicides provided no benefit.
4) Boric Acid and 5 Mol Borax combinations provided no benefit unless mixed with amine oxide.
5) The buffer capacity of Boric Acid and 5 Mol Borax when used with amine oxides (Barlox 12) provided substantial benefit to the performance of the 2,4-D type herbicide.

2,4-D alone, or herbicide 200:1 in combination with 5 Mol Borax and Barlox 12 amine oxide, did not produce as good a result as the 200:1 use of 5 Mol Borax, Boric Acid and Barlox 12 which had a 70% kill rate.

TABLES 4-6 describe, respectively, the preparation of the buffer system employed in the Warren, Pa. experiments reported in TABLES 7 and 8, with TABLE 5 referring to the experimental method and TABLE 6 showing a group of buffer systems pH and total Ion strengths.

TABLE 4 recites the composition of buffer systems 1-5 that were used in studies conducted in September, 2012 near Warren, Pa. Buffer systems 1-5 were prepared by dissolving the appropriate reagents into one liter of deionized water until a homogenous solution was obtained. TABLE 4 shows, in the left hand column, the number assigned to a particular buffer with column 2 containing the abbreviated name or full name of the buffers. The amount of acidic chemical per liter and basic chemical per liter appear in the next two pairs of columns.

TABLE 4

| | | Acidic Chemical (per liter) | | Basic Chemical (per liter) | |
|---|---|---|---|---|---|
| Buffer No. | Buffer System Name (Abbreviated Name) | Amount | Name | Amount | Name |
| 1 | Ammonium/Ammonia (Ammonia Buffer) | 1.0 mol | Ammonium Chloride | 0.5 mol | Sodium Hydroxide |
| 2 | Deprotonated Lysine/ Doubly Deprotonated Lysine (Lysine Buffer) | 1.0 mol | Lysine | 1.5 mol | Sodium Hydroxide |
| 3 | Potassium Phosphate Monobasic/ Potassium Phosphate Dibasic (Phosphate Buffer 1) | 0.5 mol | Potassium Phosphate Monobasic | 0.5 mol | Potassium Phosphate Dibasic |
| 4 | Potassium Bicarbonate/ Potassium Carbonate (Carbonate Buffer) | 0.5 mol | Potassium Bicarbonate | 0.5 mol | Potassium Carbonate |
| 5 | Boric Acid/Borax (Borate Buffer) | 4.0 mol | Boric Acid | 1.0 mol | Borax |

TABLE 3

| Herbicide Type Product Concentrate | Component Percent Weight of Buffered Amine Oxide Formula (June 2, 2004) [8] | | | Weed Type and Kill Rate[10] % 1 Year After |
|---|---|---|---|---|
| Dilution V/V 2,4-D[6] | Ethylene Glycol | 5 Mol Borax | Boric Acid | Barlox 12 | Application[5] Raspberry |

| Dilution V/V 2,4-D[6] | Ethylene Glycol | 5 Mol Borax | Boric Acid | Barlox 12 | Raspberry |
|---|---|---|---|---|---|
| | | | | | 0[1][2] |
| 50:1 | | | | | 50 |
| 200:1 | | | | | 0 |
| 200:1 | | | | 0.305 | 0 |
| 50:1 | | 0.088 | | 0.305 | 40 |
| 200:1 | | 0.088 | | | 0 |
| 200:1 | | | 0.074 | | 0 |
| 50:1 | | | 0.074 | 0.305 | 50 |
| 200:1 | | 0.044 | 0.037 | | 0 |
| 200:1 | | 0.044 | 0.037 | 0.305 | 70 |

The data shown in TABLE 3 shows clearly that, even at the lesser concentration of 50:1 employed with the herbicide TABLE 5 shows the experimental method employed in preparation of the pre-blended amine oxide and buffer systems. The compositions of buffer systems A and B identify the buffer system name in the first column with the next two columns providing identification of the acidic chemical and weight percent amount followed by the amount of basic chemical and the name. The last two columns provide the water weight percent and Barlox 12 (30% by weight amine oxide donor.) TABLE 5 discloses the composition of pre-blended Amine Oxide and Buffer Systems A and B that were used in the studies. Buffer systems A and B were prepared by dissolving the appropriate reagent salts in water and then adding the amine oxide donor in sufficient amount to make one liter of solution.

TABLE 5

Pre-blended Buffer Systems A and B Composition

| Buffer Letter | Buffer System Name (Abbreviated Name) | Acidic Chemical Amount (wt %) | Acidic Chemical Name | Basic Chemical Amount (wt %) | Basic Chemical Name | Water Amount (wt %) | Barlox 12 (30% by weight amine oxide) Amine oxide Donor (wt %) |
|---|---|---|---|---|---|---|---|
| A | Potassium Phosphate Dibasic/ Potassium Phosphate Tribasic (Phosphate Buffer 2) | 6.23 | Potassium Phosphate Dibasic | 3.02 | Potassium Phosphate Tribasic | 10.75 | 80.00 |
| B | Potassium Phosphate Monobasic/ Potassium Phosphate Dibasic (Phosphate Buffer 3) | 4.36 | Potassium Phosphate Monobasic | 3.13 | Potassium Phosphate Dibasic | 12.51 | 80.00 |

TABLE 6 shows the pH and total ion strength of buffer systems 1-5 and systems A and B.

TABLE 6 shows the pH and buffer total Ion strengths (Molar) for buffer systems 1-5 and A and B. The buffer systems preferably have a pH of about 5 to 12 and most preferably of about 7.5 to 10.5.

TABLE 6

Buffer System pH and Total Ion Strengths

| Buffer No. | Buffer System Name (Abbreviated Name) | pH (Buffer System) | Buffer Total Ion Strength (Molar) |
|---|---|---|---|
| 1 | Ammonium/Ammonia (Ammonia Buffer) | 9.5 | 1.05M |
| 2 | Deprotonated Lysine/ Doubly Deprotonated Lysine (Lysine Buffer) | 10.5 | 0.978M |
| 3 | Potassium Phosphate Monobasic/ Potassium Phosphate Dibasic (Phosphate Buffer 1) | 6.8 | 1.05M |
| 4 | Potassium Bicarbonate/ Potassium Carbonate (Carbonate Buffer) | 10.2 | 0.995M |
| 5 | Boric Acid/Borax (Borate Buffer) | 7.7 | 4.95M |
| A | Potassium Phosphate Dibasic/ Potassium Phosphate Tribasic/ (Phosphate Buffer 2) | 12.1 | 0.500M |

Referring to TABLE 7, it is shown that the 2,4-D herbicide employed with two different buffers, i.e., the Barlox 12 (12 carbon length buffer) designated 12 in TABLE 7 and Barlox 1218 which is a mixture of 12 and 18 carbon lengths, is shown as 1218 in this table. In a preferred embodiment in 1218 on a weight basis, the 12 carbon length will be present in an amount of about 1.3 to 2.0 times the amount of 18 carbon length and in the preferred range about 1.5 to 1.8 times the amount of 18 carbon length. The weed types and kill rates viewed ten months after application, are shown for a multiflora rose, raspberry and blackberry.

TABLE 7

Sep. 1, 2012 to Jul. 4, 2013

| Herbicide Type Product Concentrate Dilution v/v | No Buffer | Buffered Amine Oxide System Buffer Number & Amine Oxide Donor or Letter[9] | | | | | | | | | | | | | Weed Type and Kill Rate[10] % 10 Months After Application[5] | | |
|---|---|---|---|---|---|---|---|---|---|---|---|---|---|---|---|---|---|
| | | 1 | | 2 | | 3 | | 4 | | 5 | | A | | B | | | |
| 2,4-D[6] | | 12 | 1218 | 12 | 1218 | 12 | 1218 | 12 | 1218 | 12 | 1218 | 12 | 1218 | 12 | 1218 | Multiflora Rose | Raspberry | Blackberry |
| | | | | | | | | | | | | | | | | 0[(1)(2)] | 0[(1)(2)] | 0[(1)(2)] |
| | 200:1 | | | | | | | | | | | | | | | 0[(2)] | 0[(2)] | 0[(2)] |
| | 400:1 | | | | | | | | | | | | | | | 0[(2)] | 0[(2)] | 0[(2)] |
| | | 200:1 | | | | | | | | | | | | | | 0[(2)] | 0[(2)] | 0[(2)] |
| | | 400:1 | | | | | | | | | | | | | | 0[(2)] | 0[(2)] | 0[(2)] |
| 50:1 | | | | | | | | | | | | | | | | 0[(2)] | 90[(2)] | 90[(2)] |
| 100:1 | | | | | | | | | | | | | | | | 0[(2)] | 0[(2)] | 0[(2)] |
| 200:1 | | | | | | | | | | | | | | | | 0[(2)] | 0[(2)] | 0[(2)] |
| 200:1 | | | 200:1 | | | | | | | | | | | | | 0[(2)] | 0[(2)] | 50[(2)] |
| 200:1 | | | 400:1 | | | | | | | | | | | | | 0[(2)] | 10[(2)] | 30[(2)] |
| 200:1 | | | | | 200:1 | | | | | | | | | | | 0[(2)] | 0[(2)] | 0[(2)] |
| 200:1 | | | | | 400:1 | | | | | | | | | | | 0[(2)] | 0[(2)] | 0[(2)] |
| | | | | | | 200:1 | | | | | | | | | | 0[(2)] | 0[(2)] | 0[(2)] |
| | | | | | | 400:1 | | | | | | | | | | 0[(2)] | 0[(2)] | 0[(2)] |

TABLE 7-continued

Sep. 1, 2012 to Jul. 4, 2013

| Herbicide Type Product Concentrate Dilution v/v | No Buffer | | Buffered Amine Oxide System Buffer Number & Amine Oxide Donor or Letter[9] | | | | | | | | | | | | | | Weed Type and Kill Rate[10] % 10 Months After Application[5] | | |
|---|---|---|---|---|---|---|---|---|---|---|---|---|---|---|---|---|---|---|---|
| | | | 1 | | 2 | | 3 | | 4 | | 5 | | A | | B | | | | |
| 2,4-D[6] | 12 | 1218 | 12 | 1218 | 12 | 1218 | 12 | 1218 | 12 | 1218 | 12 | 1218 | 12 | 1218 | 12 | 1218 | Multiflora Rose | Raspberry | Blackberry |
|  |  |  | 200:1 |  |  |  |  |  |  |  |  |  |  |  |  |  | 0[2] | 0[2] | 0[2] |
|  |  |  |  | 400:1 |  |  |  |  |  |  |  |  |  |  |  |  | 0[2] | 0[2] | 0[2] |
| 200:1 |  |  | 400:1 |  |  |  |  |  |  |  |  |  |  |  |  |  | 0[2] | 90[2] | 60[2] |
| 200:1 |  |  |  |  | 200:1 |  |  |  |  |  |  |  |  |  |  |  | 60[2] | 90[2] | 90[2] |
| 200:1 |  |  |  |  |  | 400:1 |  |  |  |  |  |  |  |  |  |  | 40[2] | 90[2] | 90[2] |
|  |  |  |  |  | 200:1 |  |  |  |  |  |  |  |  |  |  |  | 0[2] | 0[2] | 0[2] |
|  |  |  |  |  |  | 400:1 |  |  |  |  |  |  |  |  |  |  | 0[2] | 0[2] | 0[2] |
|  |  |  |  |  |  |  | 200:1 |  |  |  |  |  |  |  |  |  | 0[2] | 0[2] | 0[2] |
|  |  |  |  |  |  |  |  | 400:1 |  |  |  |  |  |  |  |  | 0[2] | 0[2] | 0[2] |
| 200:1 |  |  |  |  |  |  | 200:1 |  |  |  |  |  |  |  |  |  | 100[2] | 50[2] | 100[2] |
| 200:1 |  |  |  |  |  |  |  | 400:1 |  |  |  |  |  |  |  |  | 90[2] | 90[2] | 90[2] |
| 200:1 |  |  |  |  |  |  |  |  | 200:1 |  |  |  |  |  |  |  | 80[2] | 90[2] | 70[2] |
| 200:1 |  |  |  |  |  |  |  |  |  | 400:1 |  |  |  |  |  |  | 60[2] | 90[2] | 30[2] |
|  |  |  |  |  |  |  |  |  | 200:1 |  |  |  |  |  |  |  | 0[2] | 0[2] | 0[2] |
|  |  |  |  |  |  |  |  |  |  | 400:1 |  |  |  |  |  |  | 0[2] | 0[2] | 0[2] |
|  |  |  |  |  |  |  |  |  |  |  | 200:1 |  |  |  |  |  | 0[2] | 0[2] | 0[2] |
|  |  |  |  |  |  |  |  |  |  |  |  | 400:1 |  |  |  |  | 0[2] | 0[2] | 0[2] |
| 200:1 |  |  |  |  |  |  |  |  | 200:1 |  |  |  |  |  |  |  | 100[2] | 90[2] | 100[2] |
| 200:1 |  |  |  |  |  |  |  |  |  | 400:1 |  |  |  |  |  |  | 50[2] | 60[2] | 40[2] |
| 200:1 |  |  |  |  |  |  |  |  |  |  | 200:1 |  |  |  |  |  | 100[2] | 100[2] | 80[2] |
| 200:1 |  |  |  |  |  |  |  |  |  |  |  | 400:1 |  |  |  |  | 90[2] | 100[2] | 100[2] |
|  |  |  |  |  |  |  |  |  |  |  |  | 200:1 |  |  |  |  | 0[2] | 0[2] | 0[2] |
|  |  |  |  |  |  |  |  |  |  |  |  |  | 400:1 |  |  |  | 0[2] | 0[2] | 0[2] |
|  |  |  |  |  |  |  |  |  |  |  |  |  |  | 200:1 |  |  | 0[2] | 0[2] | 0[2] |
|  |  |  |  |  |  |  |  |  |  |  |  |  |  |  | 400:1 |  | 0[2] | 0[2] | 0[2] |
| 200:1 |  |  |  |  |  |  |  |  |  |  | 200:1 |  |  |  |  |  | 30[2] | 100[2] | 100[2] |
| 200:1 |  |  |  |  |  |  |  |  |  |  |  | 400:1 |  |  |  |  | 30[2] | 30[2] | 70[2] |
| 200:1 |  |  |  |  |  |  |  |  |  |  |  |  | 200:1 |  |  |  | 100[2] | 100[2] | 90[2] |
| 200:1 |  |  |  |  |  |  |  |  |  |  |  |  |  | 400:1 |  |  | 100[2] | 90[2] | 9[2] |
|  |  |  |  |  |  |  |  |  |  |  |  |  |  | 200:1 |  |  | 0[2] | 0[2] | 0[2] |
|  |  |  |  |  |  |  |  |  |  |  |  |  |  |  | 400:1 |  | 0[2] | 0[2] | 0[2] |
|  |  |  |  |  |  |  |  |  |  |  |  |  |  |  | 200:1 |  | 0[2] | 0[2] | 0[2] |
|  |  |  |  |  |  |  |  |  |  |  |  |  |  |  |  | 400:1 | 0[2] | 0[2] | 0[2] |
| 200:1 |  |  |  |  |  |  |  |  |  |  |  |  | 160:1 |  |  |  | 50[2] | 50[2] | 50[2] |
| 200:1 |  |  |  |  |  |  |  |  |  |  |  |  |  | 320:1 |  |  | 50[2] | 50[2] | 50[2] |
|  |  |  |  |  |  |  |  |  |  |  |  |  | 160:1 |  |  |  | 0[2] | 0[2] | 0[2] |
|  |  |  |  |  |  |  |  |  |  |  |  |  |  | 320:1 |  |  | 0[2] | 0[2] | 0[2] |
| 200:1 |  |  |  |  |  |  |  |  |  |  |  |  |  |  | 160:1 |  | 0[2] | 100[2] | 100[2] |
| 200:1 |  |  |  |  |  |  |  |  |  |  |  |  |  |  |  | 320:1 | 0[2] | 100[2] | 100[2] |
|  |  |  |  |  |  |  |  |  |  |  |  |  |  |  | 160:1 |  | 0[2] | 0[2] | 0[2] |
|  |  |  |  |  |  |  |  |  |  |  |  |  |  |  |  | 320:1 | 0[2] | 0[2] | 0[2] |

The columns under the heading Buffered Amine Oxide System correspond to the identification provided in TABLES 4 through 6.

In general, in the present invention, amine oxides were mixed with buffers and then added to the herbicide formulations. Among the preferred amine oxides were those of 12 carbon length such as that sold under the trade designation Barlox 12 and a mixture of the 12 and 18 carbon lengths sold under the trade designation Barlox 1218. The buffer solution serves to stabilize the pH at a nearly constant value in a wide variety of chemical operations.

In the present invention, the buffer system maintains a substantially constant pH when in contact with biological systems. The buffer system is an aqueous system consisting of a mixture of a weak acid in its conjugate or a weak base in its conjugate acid. One may obtain the desired buffer system by directly adding the weak acid/conjugate base or weak base/conjugate acid salts or by adding the weak acid/weak base and a strong acid/strong base in sufficient amount to form the conjugate acid/conjugate base.

These concepts can be extended to polyprotic species in which more than one proton may be removed to form a different buffer systems such as phosphate systems. The preferred buffers include: ammonium salt/ammonia, Deprotonated Lysine/Doubly Deprotonated Lysine, Potassium Phosphate Monobasic/Potassium Phosphate Dibasic, Potassium Bicarbonate Potassium Carbonate, Boric Acid/Borax, Potassium Phosphate Dibasic/Potassium Phosphate Tribasic and Ammonium Citrate Tribasic. The herbicide types utilized were: 2,4-Dichlorophenoxyacetic acid dimethylamine salt (2, 4-D) (alone and mixed with other chlorophenoxy types), glyphosate (amine salts and ammonia salt types), and a blend of picrolam and triclopyr.

The tests involving the herbicides and buffered amine oxide systems were monitored over time with a kill rate at a time in the next growing season when any surviving part would normally grow. Kill was determined by determining that a plant was completely dead and decaying. Positive and negative controls were included in each study.

The amine oxide additives may be mixed as tank blends with the herbicides or may be incorporated into the herbicide formulas.

TABLE 4 shows 5 different buffers while TABLE 5 shows 2 types of amine oxide blends. TABLE 4 discloses systems wherein the appropriate reagents were dissolved in deionized water until a homogenous solution was obtained. TABLE 5 deals with the pre-blending of the amine oxide and buffer systems with the appropriate reagents salts dissolved in water and subsequently, adding the amine oxide donor.

TABLE 7 reports the tests of three different types of weeds. They are multiflora rose, raspberry and blackberry as treated with herbicide, 2,4-D in concentrations of 50:1, 100:1, 200:1 in combination with buffered amine oxide systems having of the 12 or 1218 length variety and the specific buffers indicated by the numbers 1-5 and A and B as set forth in Tables 4 through 6.

As shown in TABLE 7, amine oxides 12 and 1218 without the buffer had 0 kills for all three weeds.

As shown in TABLE 7, the concentration of 50:1 of the herbicide alone provided a high kill rate of 90% on the raspberry and blackberry target weeds, but no kill on the multiflora rose. Concentrations of 100:1 and 200:1 of the herbicide without the amine oxide system produced no kills on any of the three tested weeds.

Buffer No. 1 in the buffered amine oxide of 12 carbon length (Barlox-12) 12 column when used with 2,4-D, at the 200:1 concentration showed a 50% kill on blackberry and the 400:1 concentration showed a 10% kill on raspberry and 30% kill on blackberry. The buffered amine oxide mixed 12 and 18 carbon length (Barlox 1218) 1218 column with the buffer amine oxide system 1 showed no kills at concentrations of 200:1 and 400:1 in both the 12 and the 1218 categories when each was combined with the 2,4-D herbicide. When buffered amine oxide system 1 in both the 12 and 1218 categories was employed without the herbicide 2,4-, in concentrations of 200:1 and 400:1 respectively, no kills were experienced.

Where buffer system 2 was employed in combination with 200:1, 2,4-D in the 12 category with 400:1 concentration there was no kill of multiflora rose, 90% kill of raspberry and 60% kill of blackberry. With 200:1 1218 length, there were kills respectively of 60%, 90% and 90% and with 400:1 there were kills respectively of 40%, 90%, 90%.

Buffer amine system No. 3 in the 12 carbon length category had concentrations of 200:1 showed 100% kill of the multiflora rose, 50% kill of the raspberry and 100% kill of the blackberry. When used with 400:1 concentration, there was 90% kill on the multiflora rose, 90% kill on blackberry and 90% kill on the raspberry. In the 1218 category for buffered amine oxide system No. 3, the 200:1 concentration resulted in kills of the multiflora rose of 80%, raspberry 90% and blackberry 70%. When this was diluted to 400:1, the respective kill rates were 60%, 90% and 30%.

Buffered amine oxide No. 4 was the best performer and was superior to buffered amine oxide No. 3 in most categories.

When the buffered amine oxide system No. 4 was employed without the 2,4-D in both the 12 and 1218 categories, no kills were experienced for any of the three categories of weeds tested. When buffered amine oxide system No. 4 was employed with the 2,4-D herbicide, the 12 embodiment had kills respectively of 100%, 90% and 100% and, at the 400:1 concentration, had kills of 50, 60 and 40. With the 1218 carbon length use in buffered amine oxide system, at 200:1 there were kills at 100% for the multiflora rose and raspberry and 80% for the blackberry. At concentrations of 400:1, the kill rate as to the multiflora rose dropped to 90%, the raspberry remained at 100% and the blackberry, went to 100%. When the buffered amine oxide system No. 4 was employed alone in concentrations of 200:1 and 400:1 with both the 12 and 1218, no kills were experienced with any of the weeds.

In buffered amine oxide system No. 5, with the 12 carbon length and the 2,4-D herbicide at concentration of 200:1, there was 30% kill for the multiflora rose and 100% for both the raspberry and blackberry. When the concentration was diluted to 400:1, the multiflora rose remained at 30% kill, the raspberry kill dropped to 30% and the blackberry dropped to 70%. With respect to the same amine oxide system and 1218 carbon length at a concentration of 200:1, the kill with respect to multiflora rose and raspberry was 100% and blackberry 90%. When the concentration was reduced to 400:1, the kills were respectively 100%, 90% and 90%. These same amine oxide system No. 5 in concentrations of 200:1 and 400:1, as to both the 12 and 1218 carbon lengths without the 2,4-D, showed 0 kills in all three categories of weed. These results reaffirm the conclusion that the combination of the herbicide in a reduced concentration with the buffered amine systems produces effective weed kills while using less herbicide.

Systems A and B were pre-blended. The buffered amine oxide system A with the carbon length of 12 in concentration of 160:1 in combination with 200:1, 2-4-D, produced 50% kill on all three weeds. The same kill rate was obtained when the concentration was decreased to 320:1. When the buffered amine oxide system with 12 was employed without the 2,4-D, no kills were achieved at either concentration of the buffer system.

With regard to the B buffered amine oxide system which employed a mixture of 12 and 18 carbon lengths, when combined with 2,4-D at 200:1 concentration and either 160:1 or 320:1 concentration, no kills were experienced with respect to the multiflora rose, but 100% kills were experienced with the raspberry and blackberry.

Summarizing the data supported by TABLES 4 through 6 and reported in TABLE 7, it will be seen that the control group produced no kills on the multiflora rose, raspberry or blackberry. The 50:1 concentration of 2,4-D without the buffered amine oxide system produced no kill on the multflora rose and 90% kill on the raspberry and blackberry. Use of the 2,4-D herbicide in concentrations of 200:1 without the buffered amine oxide system, produced no kills. When, however, the 200:1 concentration of the 2,4-D herbicide was employed with the buffered amine oxides of either the 12 length or 1218 carbon length in concentrations of 200:1 or 400:1, there was substantial improvement in kill rate depending upon which buffered amine oxide system was employed and which weed was sought to be killed. In general, this shows that by combining the herbicide with the buffered amine oxide system, a synergistic effect is obtained such that a smaller amount of the herbicide needed to be used and the result was a greater kill rate as to some or all of the weeds. This was true in the 12 carbon length of buffered amine oxide system 1 and was also true of the both the 12 and 1218 carbon length systems of system 2. The same was true as to concentrations of 200:1 and 400:1 in system 3 as well as system 5 and system 6. Systems A and systems B employed 160:1 and 320:1 concentrations of the buffered amine oxide. The pH of the buffer systems were in the range of about 5 to 12 and, preferably, in the range of about 7.7 to 10.5.

Looking at the 10 combinations of buffer in buffers 1 through 5 used in combination with 200:1 concentration of 2,4-D, nine of the ten combinations produced greatly enhanced kill rates. None of the buffered amine oxide combinations controls provided any kill without the use of 200:1 2,4-D herbicide. Both of the pre-blended buffer amine oxide systems provided greatly enhanced kill when used with 200:1 2,4-D.

The herbicide concentration range may be about 25:1 to 800:1 and preferably about 50:1 to 400:1. The buffered amine oxide concentration range may be about 50:1 to 400:1 and preferably about 100:1 to 800:1. The solution may have a combined herbicide and buffered amine oxide concentration on a volume to volume basis of about 50:1 to 800:1.

Turning to TABLE 8, this shows the results of testing herbicide glyphosate against grasses.

TABLE 8

Sep. 2, 2012 to Jul. 4, 2013

| Herbicide Type Product Concentrate Dilution v/v | No Buffer | Buffer 1 | | Buffer 2 | | Buffer 3 | | Buffer 4 | | Buffer 5 | | A | | B | | Weed Type and Kill Rate[10] % 10 Months After Application[5] Grasses |
|---|---|---|---|---|---|---|---|---|---|---|---|---|---|---|---|---|
| Glyphosate[7] | | 12 | 1218 | 12 | 1218 | 12 | 1218 | 12 | 1218 | 12 | 1218 | 12 | 1218 | 12 | 1218 | |
| | 200:1 | | | | | | | | | | | | | | | 0[1][3] |
| | 400:1 | | | | | | | | | | | | | | | 0[3] |
| | | 200:1 | | | | | | | | | | | | | | 0[3] |
| | | | 400:1 | | | | | | | | | | | | | 0[3] |
| 50:1 | | | | | | | | | | | | | | | | 90[3] |
| 100:1 | | | | | | | | | | | | | | | | 50[3] |
| 200:1 | | | | | | | | | | | | | | | | 20[3] |
| 200:1 | | 200:1 | | | | | | | | | | | | | | 90[3] |
| 200:1 | | | 400:1 | | | | | | | | | | | | | 50[3] |
| 200:1 | | | | 200:1 | | | | | | | | | | | | 90[3] |
| 200:1 | | | | | 400:1 | | | | | | | | | | | 80[3] |
| | | | | 200:1 | | | | | | | | | | | | 0[3] |
| | | | | | 400:1 | | | | | | | | | | | 0[3] |
| | | | | | | 200:1 | | | | | | | | | | 0[3] |
| | | | | | | | 400:1 | | | | | | | | | 0[3] |
| 200:1 | | | | | | 400:1 | | | | | | | | | | 90[3] |
| 200:1 | | | | 200:1 | | | | | | | | | | | | 90[3] |
| 200:1 | | | | | | | 400:1 | | | | | | | | | 90[3] |
| | | | | | | 200:1 | | | | | | | | | | 0[3] |
| | | | | | | | 400:1 | | | | | | | | | 0[3] |
| | | | | | | 200:1 | | | | | | | | | | 0[3] |
| | | | | | | | 400:1 | | | | | | | | | 0[3] |
| 200:1 | | | | | | | | 200:1 | | | | | | | | 100[3] |
| 200:1 | | | | | | | | | 400:1 | | | | | | | 100[3] |
| 200:1 | | | | | | | | 200:1 | | | | | | | | 100[3] |
| 200:1 | | | | | | | | | 400:1 | | | | | | | 100[3] |
| | | | | | | | | 200:1 | | | | | | | | 0[3] |
| | | | | | | | | | 400:1 | | | | | | | 0[3] |
| | | | | | | | | 200:1 | | | | | | | | 0[3] |
| | | | | | | | | | 400:1 | | | | | | | 0[3] |
| 200:1 | | | | | | | | | | 200:1 | | | | | | 90[3] |
| 200:1 | | | | | | | | | | | 400:1 | | | | | 80[3] |
| 200:1 | | | | | | | | | | 200:1 | | | | | | 80[3] |
| 200:1 | | | | | | | | | | | 400:1 | | | | | 80[3] |
| | | | | | | | | | | 200:1 | | | | | | 0[3] |
| | | | | | | | | | | | 400:1 | | | | | 0[3] |
| | | | | | | | | | | 200:1 | | | | | | 0[3] |
| | | | | | | | | | | | 400:1 | | | | | 0[3] |
| 200:1 | | | | | | | | | | | | 200:1 | | | | 80[3] |
| 200:1 | | | | | | | | | | | | | 400:1 | | | 80[3] |
| 200:1 | | | | | | | | | | | | 200:1 | | | | 50[3] |
| 200:1 | | | | | | | | | | | | | 400:1 | | | 50[3] |
| | | | | | | | | | | | | 200:1 | | | | 0[3] |
| | | | | | | | | | | | | | 400:1 | | | 0[3] |
| | | | | | | | | | | | | 200:1 | | | | 0[3] |
| | | | | | | | | | | | | | 400:1 | | | 0[3] |
| 200:1 | | | | | | | | | | | | | | 160:1 | | 30[3] |
| 200:1 | | | | | | | | | | | | | | 320:1 | | 30[3] |
| | | | | | | | | | | | | | 160:1 | | | 0[3] |
| | | | | | | | | | | | | | 320:1 | | | 0[3] |
| 200:1 | | | | | | | | | | | | | | | 160:1 | 30[3] |
| 200:1 | | | | | | | | | | | | | | | 320:1 | 30[3] |
| | | | | | | | | | | | | | | 160:1 | | 0[3] |
| | | | | | | | | | | | | | | 320:1 | | 0[3] |

See Table 1 Footnotes
NOTE:
50.2% glyphosate isopropylamine salt used instead of 27% concentrate
NOTE:
The different buffer Systems, Amine Oxides, and Pre-blended System as shown in Tables 4, 5 and 6

Referring to TABLE 8, there is shown a series of tests with the materials shown in TABLES 4, 5 and 6. The Glyphosate herbicide used in the tests reported in TABLE 8 were 50.2% Glyphosate Isopropylamine salt instead of the 27% concentrate. The tested grasses were mixed fesques and crab grasses.

As shown in TABLE 8, the tests performed with no buffer and no herbicide in concentrations of 200:1 and 400:1 produced no killing of grass. The herbicide alone in a concentration of 50:1 killed 90% of the grass. In a concentration of 100:1, the herbicide alone killed 50% of the grass, and in a concentration of 200:1, killed 20% of the grass.

When buffered amine oxide system No. 1 was employed in a concentration of 200:1 in combination with the Glyphosate of 200:1, 90% of the grass was killed. In all of the tests appearing below in TABLE 8, the Glyphosate was used in a concentration of 200:1. When amine oxide system 1 was employed in the concentration of 400:1 with the Glyphosate, the kill rate of the grass was 50% 12 length version. There were similar numbers with the 1218 at 200:1 were 90% and 400:1, 80%. When amine oxide system No. 1 was employed in 12 and 1218 without the Glyphosate, there was no killing of grass.

When buffered amine oxide system No. 2 was employed in the 12 version at 400:1, 90% of the grass was killed with the 12 version and 90% was killed at 200:1 and 400:1 with the 1218 version. Use of amine oxide system No. 2 alone in both the 12 and 1218 carbon lengths, respectively, at 200:1 and 400:1, killed no grass. It is the combination of the Glyphosate and the buffered amine oxide system which resulted in the desired high level of grass kills. Looking at buffered amine oxide system No. 3 in concentrations of 200:1 and 400:1 for the 12 version, and 200:1 and 400:1 in the 1218 version, there was 100% destruction of the grass. The buffered amine oxide system No. 3, when employed in both the 12 and 1218 version without the Glyphosate, resulted in no killing of grass.

When amine oxide system No. 4 in combination with the Glyphosate at the 200:1 level, 90% of the grass was killed and at the 400:1 level, 80% was killed, both in the 12 version. In the 1218 version, at 200:1 and 400:1, the kill rate was 80%. Use of this amine oxide system without the Glyphosate in both the 12 and 1218 versions, produced no kill of grass.

The amine oxide system No. 5, when employed in the 12 version at 200:1 and 400:1, resulted in 80% grass kill and, in the 1218 at both the 200:1 and 400:1 concentration, resulted in 50% grass kill. Use of this amine oxide system without the Glyphosate in both the 12 and 1218 versions, produced no grass killing. With regard to amine oxide system A in combination with the Glyphosate at both concentrations 160:1 and 320:1, there was a 30% grass kill and, in the same respective concentrations without the use of Glyphosate, there was no grass kill. With regard to amine oxide system B in the 160:1 and 320:1 concentrations in combination with the Glyphosate, there was, in each case, 30% kill and use of this alone resulted in no grass kill.

The formulations employed in the New Zealand tests used the following materials:
Glyphosate 88WSG (a wettable powder)
Glyphosate 80% w/w (Active Ingredient)
Ammonia 8.2% w/w (Neutralizer)
Proprietary non-ionic Surfactant 11.8% w/w
2,4-D Amine 800WDG
2,4-D Acid 80.0% w/w (Active Ingredient)
Dimethylamine 17.0% w/w (Neutralizer)
Proprietary Surfactant Up to 13.0% w/w
Picloram 20G
Picloram amine salt 3% w/w (Active Ingredient)
Dye <0.1% w/w
Inert Granule Agent Up to 100% w/w
Trichloram Brushkiller
Triclopyr BEE (95% active) 41.7% w/v (Active Ingredient)
Picloram Acid 10% w/v (Acid Ingredient)
Proprietary amine 5 to 10% w/v (Neutralizer, based on in-process pH)
Proprietary emulsifier 10 to 15% w/v
Glycol Ether DE Up to 100% w/v Solvent In the United States tests, the materials were applied to the plants by a low volume hand volume metric sprayer. In the New Zealand tests, a conventional farm boom sprayer was employed to distribute the materials.

In the New Zealand tests, four acres were employed. The first acre of grass pasture was sprayed with 2,4-D type herbicide at the label rate dilution and label rate application. A second acre was sprayed with a tank mix of 2,4-D herbicide at one-half the label rate of dilution plus the buffered amine oxide formula diluted 200:1. A third acre was sprayed with Glyphosate herbicide at label dilution rate and label application rate. Finally, a fourth acre was sprayed with a mix of Glyphosate at one-half the label rate dilution plus the buffered amine oxide formula diluted 200:1. Inspection after 13 months after application of the pasture sprayed with only 2,4-D had a total of weed kill of only 50% compared to adjacent unsprayed acre of control pasture. The pasture sprayed with 2,4-D and buffered amine oxide formula had an 80% target weed kill rate. After 13 months, the pasture sprayed with only Glyphosate had a total grass kill of 30% compared to the adjacent unsprayed acre of control pasture. The pasture sprayed with Glyphosate and buffered amine oxide had a 70% kill rate.

A further test in New Zealand was conducted on 40 wilding Radiata pines with a low volume hand sprayer. Twenty wilding pines were sprayed with a local picrolam type herbicide at label rate dilution and label rate application. Another 20 wilding pines were sprayed with a tank mix of picrolam at one-half the label rate dilution plus the buffered amine oxide formula diluted 200:1. After four months, the wilding pines sprayed with only picrolam had a kill rate of 40% compared to the adjacent wilding pine unsprayed controls while those sprayed with picrolam and buffered amine oxide with had a 80% kill rate.

The results of these tests are tabulated in TABLES 9 through 14. It was found that that using an amine oxide in the Potassium Bicarbonate/Potassium Carbonate Buffer system with Glyphosate at the lowest label recommendation was most productive. The buffered amine oxide additive to Glyphosate significantly outperformed the standalone herbicide at each of the readings. The 2,4-Dichlorophenoxyacetic acid dimethylamine salt with amine oxide and the Potassium Bicarbonate/Potassium Carbonate buffer system outperformed the standalone herbicide on ferns. The second best buffered amine oxide was Potassium Phosphate Monobasic/Potassium Phosphate Dibasic with amine oxide when the combination with the same herbicide against the same target organisms. Other buffers tested shows significant ability to increase the performance of all types of herbicide tested.

TABLE 9

February 2013 to November 2013

| Herbicide Type Product Concentrate Dilution v/v | No Buffer | | Buffered Amine Oxide System Buffer Number & Amine Oxide Donor or Letter[8][9] | | | | | | | | | | | | | Weed Type and Kill Rate[10] % 240 Days After Application[4] | | |
|---|---|---|---|---|---|---|---|---|---|---|---|---|---|---|---|---|---|---|
| | | | 1 | | 2 | | 3 | | 4 | | 5 | | 6 | | 8 | | | |
| 2,4-D[6] | 12 | 1218 | 12 | 1218 | 12 | 1218 | 12 | 1218 | 12 | 1218 | 12 | 1218 | 12 | 1218 | 1218 | Broom | Fern | Gorse |
| | | | | | | | | | | | | | | | | 0[1][3] | 0[1][2] | 0[1][3] |
| | 200:1 | | | | | | | | | | | | | | | 0 | 0 | 0 |
| | | 400:1 | | | | | | | | | | | | | | | | |
| | | | 200:1 | | | | | | | | | | | | | 0 | 0 | 0 |
| | | | | 400:1 | | | | | | | | | | | | | | |
| 50:1 | | | | | | | | | | | | | | | | 50 | 60 | 50 |
| 100:1 | | | | | | | | | | | | | | | | 30 | 20 | 30 |
| 150:1 | | | | | | | | | | | | | | | | 20 | 10 | 0 |
| 200:1 | | | 200:1 | | | | | | | | | | | | | | | |
| 200:1 | | | | 400:1 | | | | | | | | | | | | | | |
| 200:1 | | | | | 200:1 | | | | | | | | | | | | | |
| 200:1 | | | | | | 400:1 | | | | | | | | | | | | |
| | | | | | 200:1 | | | | | | | | | | | | | |
| | | | | | | 400:1 | | | | | | | | | | | | |
| | | | | | | | 200:1 | | | | | | | | | | | |
| | | | | | | | | 400:1 | | | | | | | | | | |
| 200:1 | | | | | | | 400:1 | | | | | | | | | | | |
| 200:1 | | | | | | | | 200:1 | | | | | | | | | | |
| 200:1 | | | | | | | | 400:1 | | | | | | | | 100 | | |
| | | | | | | | | | 200:1 | | | | | | | 0 | | |
| | | | | | | | | | | 400:1 | | | | | | | | |
| | | | | | | | | | | | 200:1 | | | | | | | |
| | | | | | | | | | | | | 400:1 | | | | | | |
| 200:1 | | | | | | | | | 200:1 | | | | | | | 100 | | |
| 200:1 | | | | | | | | | | 400:1 | | | | | | 100 | | |
| 200:1 | | | | | | | | | | | 200:1 | | | | | | | |
| 200:1 | | | | | | | | | | | | 400:1 | | | | | | 90 |
| | | | | | | | | | | | | | 200:1 | | | | | |
| | | | | | | | | | | | | | | 400:1 | | | | |
| | | | | | | | | | | | | | | 200:1 | | | | |
| | | | | | | | | | | | | | | | 400:1 | | | |
| 200:1 | | | | | | | | | | | | 200:1 | | | | 100 | 100 | 100 |
| 200:1 | | | | | | | | | | | | | 400:1 | | | 100 | 100 | |
| 200:1 | | | | | | | | | | | | | | 200:1 | | 100 | 100 | |
| 200:1 | | | | | | | | | | | | | | | 400:1 | 100 | 100 | |
| | | | | | | | | | | | | | | 200:1 | | 0 | 0 | 0 |
| | | | | | | | | | | | | | | | 400:1 | | | |
| | | | | | | | | | | | | | | | 200:1 | 0 | 0 | 0 |
| | | | | | | | | | | | | | | | 400:1 | | | |
| 200:1 | | | | | | | | | | | | | | 200:1 | | | 30 | |
| 200:1 | | | | | | | | | | | | | | | 400:1 | 50 | 30 | 40 |
| 200:1 | | | | | | | | | | | | | | | 200:1 | 40 | 50 | |
| 200:1 | | | | | | | | | | | | | | | 400:1 | 60 | | 60 |
| | | | | | | | | | | | | | | | 200:1 | | | |
| | | | | | | | | | | | | | | | 400:1 | | | |
| | | | | | | | | | | | | | | | 200:1 | | | |
| | | | | | | | | | | | | | | | 400:1 | | | |
| 200:1 | | | | | | | | | | | | | | 200:1 | | | | |
| 200:1 | | | | | | | | | | | | | | | 400:1 | | | |
| 200:1 | | | | | | | | | | | | | | | 200:1 | | | |
| 200:1 | | | | | | | | | | | | | | | 400:1 | 60 | | |
| 200:1 | | | | | | | | | | | | | | | 160:1 | | | |

TABLE 9-continued

February 2013 to November 2013

| Herbicide Type Product Concentrate Dilution v/v | No Buffer | Buffered Amine Oxide System Buffer Number & Amine Oxide Donor or Letter[8][9] | | | | | | | | | | | | | Weed Type and Kill Rate[10] % 240 Days After Application[4] | | |
|---|---|---|---|---|---|---|---|---|---|---|---|---|---|---|---|---|---|
| | | 1 | | 2 | | 3 | | 4 | | 5 | | 6 | | 8 | | | |
| 2,4-D[6] | 12 | 1218 | 12 | 1218 | 12 | 1218 | 12 | 1218 | 12 | 1218 | 12 | 1218 | 12 | 1218 | 1218 | Broom | Fern | Gorse |
| 200:1 | | | | | | | | | | | | | | | 320:1 160:1 320:1 | | | |

[1]Water controls
[2]10 plants: 20 milliliter applied per plant
[3]200 milliliter per plant
[4]Low volume hand applied spray
5) Commercial concentrate containing 100 gram per liter picloram amine salt and, 300 gram per liter triclopyr butoxy ethyl ether
[6]Commercial concentrate containing 800 gram per kilogram 2,4-D Dimethylamine salt
7) Commercial concentrate containing 800 gram per kilogram glyphosate ammonium salt
[8]Buffers, amine oxides, and pre-blended systems are shown in Tables 4, 5, and 6 with exception that pre-blend A was not tested and a different Buffer shown in Tables 10 and 11 was added as Buffer No. 6
[9]Buffers and amine oxides were added to dilute herbicide solutions, volume to volume
[10]No activity of a living plant: dead and decaying

TABLE 10

Buffer System 6 Composition

| Buffer No. | Buffer System Name (Abbreviated Name) | Acidic Chemical (per liter) | | Basic Chemical (per liter) | |
|---|---|---|---|---|---|
| | | Amount | Name | Amount | Name |
| 6 | Ammonium/Citrate Tribasic (Ammonia Citrate Tribasic Buffer) | 3.0 mol | Ammonium | 1.0 mol | Citrate |

TABLE 11

Buffer System pH and Total Ion Strengths

| Buffer No. | Buffer System Name (Abbreviated Name) | pH (Buffer System) | Buffer Total Ion Strength (Molar) |
|---|---|---|---|
| 6 | Ammonium/Citrate Tribasic (Ammonia Citrate Tribasic Buffer) | 6.8 | 4.00M |

Turning to TABLE 9, the buffered amine oxides and pre-blended systems shown in TABLES 4, 5 and 6 were employed in these tests with the exception that pre-blend A was substituted for the buffer 6 shown in TABLES 10 and 11. The tests were performed against the weeds, broom, fern and gorse.

Referring to Footnotes 2 and 3 of TABLE 9, the quantities of the solution applied to the plants were either 20 milliliters per plant (Footnote 2) or 200 milliliters per plant (Footnote 3).

The 2,4-D herbicide was the commercial concentrate containing 8 grams per kilogram of 2,4-D. The no buffer category as to both the 12 and 1218 in concentrations 200:1 and 400:1 provided no weed kill. The herbicide 2,4-D used alone at a concentration of 50:1 had 50% kill on broom, 60% kill on fern and 50% kill on gorse. At 100:1 concentration, this kill rate was reduced respectively to 30%, 20% and 30% and at concentration 150:1, this kill rate was reduced to 20%, 10%, and 0%.

In table 9 where there was use of 2,4-D alone in concentrations of 50:1, 100:1, 150:1, there was, starting with the 50:1, killings of 50, 60 and 50 and, with the next two, reduced amounts. In connection with buffered amine oxide system no. 2 with the 1218 in a 400:1 concentration as in combination with the 2,4-d, there was 100% killing of broom. In connection with buffered amine oxide system no. 3 at both the 200:1 and the 400:1 concentrations, there was 100% kill on the broom and with the 1218 at 400:1, there was a 90% kill of gorse.

Buffered amine oxide system no. 4 as to both the 12 and the 1218 had a very impressive 100% kill as to broom and fern and 100% kill as to the 200:1 on the gorse.

TABLES 10 and 11 show properties of Buffer No. 6.

TABLE 12 shows the use of 2,4-D in testing a number of buffered amine oxide systems as against the New Zealand blackberry which is different from the North American blackberry. The buffer systems in TABLE 5, 12 through 14 are the same as those identified by the same numbers and letters in TABLES 4 through 6. The amine oxide without buffer as to both 12 and 1218 in concentrations of 200:1 and 400:1 produced 0 kills. It will be noted that 2,4-D in concentrations of 50:1, 100:1 and 150:1 without a buffer amine oxide system had no kills. When the 2,4-D was combined with 200-1 carbon 12, 20 kills occurred and with 400-1, ten kills occurred. When it was used with 1218 carbon length, the 200:1 concentration provided 30 kills. The buffered amine oxide system No. 2, when combined with 2,4-D with both having 200:1 concentration, had 40 kills. Buffered amine oxide system No. 3 with the 1218 length at the 200:1 concentration combined with the 200-1 2,4-D concentration, had 100 kills and the buffering system, and with 400-1, had 90 kills. With respect to buffer amine oxide 4 and the combination of 200:1 2,4-D, and both the 12 length and 1218 length at both concentrations of 200:1 and 400:1, there was 100% kill.

Referring to TABLE 13, which reports tests of Glyphosate against gorse and blackberry, the no buffer test produced no kills. At a 25:1 concentration, the Glyphosate alone had kills of gorse and blackberry, respectively, of 80 and 90. At 30:1, the kills were at 40 in both categories, and at 50:1, the kills were 10% for gorse and 20% for blackberry. At 100:1 herbicide, the buffered amine oxide system 1 at a length of 12 for 200:1 concentration, had a kill rate of 70% and at 200:1 concentration of 1218, had a kill rate of 90%. At 100:1 of glyphosate and 200:1 12 length, buffered amine oxide system No. 4 had 100% kill of both gorse and blackberry. At 400:1, both the 12 and 1218 length, the respective killing was 90% and 100% and, at 1218 200:1, it was 90%.

Referring to TABLE 14 which employed Picloram and Triclopyr as the herbicides, and broom, fern and gorse as the weeds being challenged, at a 50:1 concentration, the herbicide alone killed 60%, 30% and 30% of the respective weeds. At 100:1, these percentages dropped to 30%, 40%, 30% and at 150:1, they dropped to 0%, 20%, 20%. When used in combination with buffered amine oxide system No. 1 at the 12 length diluted 200:1 it produced a kill of 40% on the broom and 70% on gorse and at the 400:1 percent at the 12 level, killed 60% of gorse. With regard to the 1218 length of No. 1 at 200:1, the kill percentage was 50%, and 400:1, it was 60%. With a 200:1 concentration of the herbicide, and 200:1 concentration of buffered amine oxide system No. 3, length 12, 100% of the broom was killed and at 400:1 of buffer No. 3, 100% of the broom was killed. At the 1218 length of system No. 3 at 200:1 concentration, 100% of the broom was killed and 90% of the gorse with the identical result being received for the same system and length at a concentration of 400:1.

The combination of the herbicide with amine oxide buffer system No. 4 at the 1218 length at a concentration of 200:1 produced 100% destruction of fern and gorse and at the 400:1 concentration, 100% destruction of the fern and gorse.

TABLE 12

February 2013 to November 2013

| Herbicide Type Product Concentrate | | Buffered Amine Oxide System Buffer Number & Amine Oxide Donor or Letter[8][9] | | | | | | | | | | | | | Weed Type and Kill Rate[10] % 240 Months |
|---|---|---|---|---|---|---|---|---|---|---|---|---|---|---|---|
| Dilution v/v | No Buffer | 1 | | 2 | | 3 | | 4 | | 5 | | 6 | | 8 | After Application[4] |
| 2,4-D[6] | | 12 | 1218 | 12 | 1218 | 12 | 1218 | 12 | 1218 | 12 | 1218 | 12 | 1218 | 1218 | Blackberry |
| | | | | | | | | | | | | | | | 0[1][2] |
| | 200:1 | | | | | | | | | | | | | | 0 |
| | 400:1 | | | | | | | | | | | | | | |
| | | 200:1 | | | | | | | | | | | | | 0 |
| | | 400:1 | | | | | | | | | | | | | |
| 50:1 | | | | | | | | | | | | | | | 0 |
| 100:1 | | | | | | | | | | | | | | | 0 |
| 150:1 | | | | | | | | | | | | | | | 0 |
| 200:1 | | 200:1 | | | | | | | | | | | | | 20 |
| 200:1 | | 400:1 | | | | | | | | | | | | | 10 |
| 200:1 | | | 200:1 | | | | | | | | | | | | 30 |
| 200:1 | | | 400:1 | | | | | | | | | | | | |
| | | | | 200:1 | | | | | | | | | | | |
| | | | | | 200:1 | | | | | | | | | | |
| 200:1 | | | | | 400:1 | | | | | | | | | | |
| 200:1 | | | | | | 200:1 | | | | | | | | | 40 |
| 200:1 | | | | | | 400:1 | | | | | | | | | |
| | | | | | | | 200:1 | | | | | | | | |
| | | | | | | | | 200:1 | | | | | | | |
| 200:1 | | | | | | | 200:1 | | | | | | | | |
| 200:1 | | | | | | | 400:1 | | | | | | | | |
| 200:1 | | | | | | | | 200:1 | | | | | | | 100 |
| 200:1 | | | | | | | | 400:1 | | | | | | | 90 |
| | | | | | | | | | 200:1 | | | | | | |
| | | | | | | | | | | 200:1 | | | | | |
| 200:1 | | | | | | | | | 200:1 | | | | | | 100 |
| 200:1 | | | | | | | | | | 400:1 | | | | | 100 |
| 200:1 | | | | | | | | | | 200:1 | | | | | 100 |
| 200:1 | | | | | | | | | | 400:1 | | | | | 100 |
| | | | | | | | | | | | 200:1 | | | | |
| | | | | | | | | | | | | 200:1 | | | |
| 200:1 | | | | | | | | | | | 200:1 | | | | |
| 200:1 | | | | | | | | | | | | 400:1 | | | |
| 200:1 | | | | | | | | | | | | 200:1 | | | 90 |
| 200:1 | | | | | | | | | | | | 400:1 | | | |
| | | | | | | | | | | | | | 200:1 | | |
| | | | | | | | | | | | | | | 200:1 | |
| 200:1 | | | | | | | | | | | | 200:1 | | | 50 |
| 200:1 | | | | | | | | | | | | | 400:1 | | |
| 200:1 | | | | | | | | | | | | | 200:1 | | |
| 200:1 | | | | | | | | | | | | | 400:1 | | |
| 200:1 | | | | | | | | | | | | | | 160:1 | |
| 200:1 | | | | | | | | | | | | | | 320:1 | 80 |
| | | | | | | | | | | | | | | 160:1 | |

TABLE 13

February 2013 to November 2013

| Herbicide Type Product Concentrate Dilution v/v Glyphosate[7] | No Buffer | | Buffered Amine Oxide System Buffer Number & Amine Oxide Donor or Letter[8][9] | | | | | | | | | | | | | Weed Type and Kill Rate[10] % 240 Days After Application[4] | |
|---|---|---|---|---|---|---|---|---|---|---|---|---|---|---|---|---|---|
| | | | 1 | | 2 | | 3 | | 4 | | 5 | | 6 | | 8 | Gorse | Black-berry |
| | 12 | 1218 | 12 | 1218 | 12 | 1218 | 12 | 1218 | 12 | 1218 | 12 | 1218 | 12 | 1218 | 1218 | | |
| | | | | | | | | | | | | | | | | 0[1][3] | 0[1][2] |
| | 200:1 | | | | | | | | | | | | | | | | |
| | | 400:1 | | | | | | | | | | | | | | | |
| | | | 200:1 | | | | | | | | | | | | | | |
| | | | | 400:1 | | | | | | | | | | | | | |
| 25:1 | | | | | | | | | | | | | | | | 80 | 90 |
| 30:1 | | | | | | | | | | | | | | | | 40 | 40 |
| 50:1 | | | | | | | | | | | | | | | | 10 | 20 |
| 100:1 | | | 200:1 | | | | | | | | | | | | | 70 | |
| 100:1 | | | | 400:1 | | | | | | | | | | | | | 90 |
| 100:1 | | | | | 200:1 | | | | | | | | | | | | |
| 100:1 | | | | | | 400:1 | | | | | | | | | | | |
| | | | | | 200:1 | | | | | | | | | | | | |
| | | | | | | 400:1 | | | | | | | | | | | |
| | | | | | | | 200:1 | | | | | | | | | | |
| | | | | | | | | 400:1 | | | | | | | | | |
| 100:1 | | | | | | 400:1 | | | | | | | | | | | 60 |
| 100:1 | | | | | | | 200:1 | | | | | | | | | | |
| 100:1 | | | | | | | | 400:1 | | | | | | | | | 70 |
| | | | | | | | 200:1 | | | | | | | | | | |
| | | | | | | | | 400:1 | | | | | | | | | |
| | | | | | | | | | 200:1 | | | | | | | | |
| | | | | | | | | | | 400:1 | | | | | | | |
| 100:1 | | | | | | | | 200:1 | | | | | | | | | |
| 100:1 | | | | | | | | | 400:1 | | | | | | | | 90 |
| 100:1 | | | | | | | | | | 200:1 | | | | | | | 90 |
| 100:1 | | | | | | | | | | | 400:1 | | | | | 90 | 90 |
| | | | | | | | | | 200:1 | | | | | | | | |
| | | | | | | | | | | 400:1 | | | | | | | |
| | | | | | | | | | | | 200:1 | | | | | | |
| | | | | | | | | | | | | 400:1 | | | | | |
| 100:1 | | | | | | | | | | 200:1 | | | | | | 100 | 100 |
| 100:1 | | | | | | | | | | | 400:1 | | | | | 90 | 100 |
| 100:1 | | | | | | | | | | | | 200:1 | | | | 90 | |
| 100:1 | | | | | | | | | | | | | 400:1 | | | 90 | 100 |
| | | | | | | | | | | | | 200:1 | | | | | |
| | | | | | | | | | | | | | 400:1 | | | | |
| | | | | | | | | | | | | | | 200:1 | | | |
| | | | | | | | | | | | | | | | | | |
| 200:1 | | | | | | | | | | | | 200:1 | | | | | |
| 200:1 | | | | | | | | | | | | | 400:1 | | | 60 | 80 |
| 200:1 | | | | | | | | | | | | | | 200:1 | | | |
| 200:1 | | | | | | | | | | | | | | | | | |
| | | | | | | | | | | | | | | 400:1 | | | |
| | | | | | | | | | | | | | 200:1 | | | | |
| | | | | | | | | | | | | | | 400:1 | | | |
| 100:1 | | | | | | | | | | | | | 200:1 | | | | |
| 100:1 | | | | | | | | | | | | | | 400:1 | | 70 | |
| 100:1 | | | | | | | | | | | | | | | 200:1 | 70 | |
| 100:1 | | | | | | | | | | | | | | | 400:1 | | |
| 200:1 | | | | | | | | | | | | | | | 160:1 | | |
| 200:1 | | | | | | | | | | | | | | | 320:1 | | |

TABLE 14

February 2013 to November 2013

| Herbicide Type Product Concentrate Dilution v/v Picloram & Triclopyr[5] | No Buffer | Buffered Amine Oxide System Buffer Number & Amine Oxide Donor or Letter[8][9] | | | | | | | | | | | | | Weed Type and Kill Rate[10] % 240 Days After Application[4] | | |
|---|---|---|---|---|---|---|---|---|---|---|---|---|---|---|---|---|---|
| | | 1 | | 2 | | 3 | | 4 | | 5 | | 6 | | 8 | | | |
| | | 12 | 1218 | 12 | 1218 | 12 | 1218 | 12 | 1218 | 12 | 1218 | 12 | 1218 | 1218 | Broom | Fern | Gorse |
| | | | | | | | | | | | | | | | 0[1][3] | 0[1][2] | 0[1][3] |
| | | 200:1 | | | | | | | | | | | | | | | |
| | | 400:1 | | | | | | | | | | | | | | | |
| | | | 200:1 | | | | | | | | | | | | | | |
| | | | 400:1 | | | | | | | | | | | | | | |
| | 50:1 | | | | | | | | | | | | | | 60 | 30 | 30 |
| | 100:1 | | | | | | | | | | | | | | 30 | 40 | 30 |
| | 150:1 | | | | | | | | | | | | | | 0 | 20 | 70 |
| | 200:1 | | | | | | | | | | | | | | 40 | | |
| | 200:1 | | 400:1 | | | | | | | | | | | | | | 70 |
| | 200:1 | | | | | | | | | | | | | | | | 60 |
| | 200:1 | | | 200:1 | | | | | | | | | | | 50 | | |
| | 200:1 | | | | 400:1 | | | | | | | | | | 60 | | |
| | | | | 200:1 | | | | | | | | | | | | | |
| | | | | | 400:1 | | | | | | | | | | | | |
| | | | | | | 200:1 | | | | | | | | | | | |
| | | | | | | | 400:1 | | | | | | | | | | |
| | 200:1 | | | | 400:1 | | | | | | | | | | | | 80 |
| | 200:1 | | | | | 200:1 | | | | | | | | | | | 80 |
| | 200:1 | | | | | | 400:1 | | | | | | | | | | |
| | | | | | | 200:1 | | | | | | | | | | | |
| | | | | | | | 400:1 | | | | | | | | | | |
| | | | | | | | | 200:1 | | | | | | | | | |
| | | | | | | | | | 400:1 | | | | | | | | |
| | 200:1 | | | | | 200:1 | | | | | | | | | 100 | | |
| | 200:1 | | | | | | 400:1 | | | | | | | | 100 | | 100 |
| | 200:1 | | | | | | | 200:1 | | | | | | | 100 | | 90 |
| | 200:1 | | | | | | | | 400:1 | | | | | | 100 | | 90 |
| | | | | | | | | 200:1 | | | | | | | | | |
| | | | | | | | | | 400:1 | | | | | | | | |
| | | | | | | | | | | 200:1 | | | | | | | |
| | | | | | | | | | | | 400:1 | | | | | | |
| | 200:1 | | | | | | | 200:1 | | | | | | | | | 100 |
| | 200:1 | | | | | | | | 400:1 | | | | | | 40 | | 90 |
| | 200:1 | | | | | | | | | 200:1 | | | | | | 100 | 100 |
| | 200:1 | | | | | | | | | | 400:1 | | | | | 100 | 100 |
| | | | | | | | | | | 200:1 | | | | | | | |
| | | | | | | | | | | | 400:1 | | | | | | |
| | | | | | | | | | | | | 200:1 | | | | | |
| | | | | | | | | | | | | | 400:1 | | | | |
| | 200:1 | | | | | | | | | 200:1 | | | | | 50 | 50 | 80 |
| | 200:1 | | | | | | | | | | 400:1 | | | | | 40 | |
| | 200:1 | | | | | | | | | | | 200:1 | | | 70 | | 80 |
| | 200:1 | | | | | | | | | | | | 400:1 | | 50 | | 80 |
| | | | | | | | | | | | | 200:1 | | | | | |
| | | | | | | | | | | | | | 400:1 | | | | |
| | | | | | | | | | | | | | | 200:1 | | | |
| | | | | | | | | | | | | | | 400:1 | | | |
| | 200:1 | | | | | | | | | | | 200:1 | | | | | 80 |
| | 200:1 | | | | | | | | | | | | 400:1 | | | | |
| | 200:1 | | | | | | | | | | | | | 200:1 | | | |
| | 200:1 | | | | | | | | | | | | | 400:1 | | | |
| | 200:1 | | | | | | | | | | | | | 160:1 | 50 | 80 | 90 |
| | 200:1 | | | | | | | | | | | | | 320:1 | | | 70 |
| | | | | | | | | | | | | | | 160:1 | | | |
| | | | | | | | | | | | | | | 320:1 | | | |

The pre-blending as in systems 1 through 5 and subsequent blending as in A and B produced similar results.

In practicing the method of the present invention, one would obtain the desired herbicide in a concentrate form in liquid or powder form and dilute it using a suitable solvent such as water to the concentration desired to be employed. One would then select the buffered amine oxide desired in concentrate form and dilute it with a suitable solvent, such as water, to achieve the concentration desired. The two solutions are then mixed in a suitable blender to achieve a homogenous solution for spraying.

The solution so created is then applied in the area of the weeds to be killed directly to the weeds. While the testing performed generally had follow-up at a follow-up review about a year later to make sure that no regrowth had occurred, it will be appreciated that, for most weeds, killing is completed within about one to two months or less after initial spraying.

The herbicide buffered amine oxide system of the present invention may be applied to the weeds by many means depending upon the nature of the weed and the quantity and location of the same. In general, spraying through a hand sprayer, a conventional agricultural sprayer or even aerial distribution from an airplane may be employed. In spraying, it will generally be desired to spray the foliage. For trees, woody plants, and some others, the solution may be injected into the plant, applied to cut surfaces of the plant or placed at the base of the plant where it will leach into the plant roots. The sprayable solution having a combined herbicide solution and buffered amine oxide solution concentration on a volume to volume basis of about 50:1 to 800:1 and preferably about 50:1 to 400:1.

It will be appreciated that the present invention may also be employed to use the herbicide and buffered amine oxide systems to destroy seeds, bulbs and roots of plants before they germinate and to apply the same to soil to resist future emergence of weeds.

It will be appreciated that while the extensive tests reported herein were performed employing the most commonly used herbicides, other herbicides may be employed, if desired.

It will be appreciated that in some instances where herbicides are employed to kill weeds and yet certain plants such as grasses which in a particular instance are not desired to be killed, an insecticide or fungicide may be blended with the solution of the present invention and applied to the plants so that the weeds will be killed by the herbicide, but a herbicide which does not kill grasses would not kill the grasses with the further benefit of the insecticide and fungicide serving to resist destruction of the grasses. The use of 2,4-D, for example, in such cases, would function in this dual role while otherwise obtaining the benefits of the weed killing aspects of the present invention along with preservation of plants which are not weeds.

While particular embodiments of this invention have been described herein for purposes of illustration, it will be evident to those skilled in the art that numerous variations of the details of the present invention may be made without departing from the invention as defined in the appended claims.

What is claimed is:

1. A method of killing weeds comprising
providing a solution having a herbicide admixed with a buffered amine oxide in water,
said solution characterized by the property of synergistically killing weeds to a greater extent than either said herbicide or said buffered amine oxide used alone, and
applying said solution to said weeds.

2. The method of killing weeds of claim 1 comprising
said solution be an aqueous solution with said herbicide having a concentration in said solution on a volume to volume basis based on the total solution volume of about 25:1 to 800:1, and
said buffered amine oxide concentration on a volume to volume basis in said solution of about 50:1 to 800:1.

3. The method of killing weeds of claim 1 comprising
said buffered amine oxide selected from the group consisting of said buffered amine oxide selected from a group consisting of Potassium Phosphate Monobasic/Potassium Phosphate Dibasic and Potassium Bicarbonate/Potassium Carbonate.

4. The method of killing weeds of claim 1 comprising
said herbicide being present in an amount generally equal to the lowest label rate for said herbicide.

5. The method of killing weeds of claim 1 comprising
applying said solution by spraying the same on said weeds.

6. The method of killing weeds of claim 1 comprising
subsequent to said spraying inspecting said weeds to confirm that the desired weed kill has been achieved.

7. The method of killing weeds of claim 5 comprising
applying said spray by at least one method selected from the group consisting of manual spraying, automated pump spraying, and
aerial spraying.

8. The method of killing weeds of claim 1 comprising
effecting said spraying in regions where weeds are closely adjacent to plants which will not be killed by said solution.

9. The method of claim 6 wherein
said inspection is effected visually.

10. The method of claim 2 wherein
said herbicide has a concentration of about 50:1 to 400:1 and said buffered amine oxide has a concentration of about 100:1 to 400:1.

11. The method of claim 1 wherein
said herbicide is selected from the group consisting of 2,4-D, glyphosate, picrolam, tricolipyr and combinations thereof.

12. The method of claim 1 comprising
said buffer amine oxide being selected from the group consisting of weak acid and its conjugate base and a weak base and its conjugate acid.

13. The method of claim 12 comprising
said buffered amine oxide being selected from the group consisting of ammonium salt/ammonia, Deprotonated Lysine/Doubly Deprotonated Lysine, Potassium Phosphate Monobasic/Potassium Phosphate Dibasic, Potassium Bicarbonate/Potassium Carbonate, Boric Acid/Borax, Potassium Phosphate Dibasic/Potassium Phosphate Tribasic and Ammonium Citrate Tribasic.

14. The method of claim 1 wherein
said buffered amine oxide has a pH of about 5 to 12.

15. The method of claim 1 wherein
said buffered amine oxide has a pH of about 7.5 to 10.2.

16. The method of claim 1 comprising
said buffered amine oxides selected from the group consisting of
(a) 12 carbon length amine oxides and (b) a mixture of 12 and 18 carbon length amine oxides.

17. The method of claim 11 comprising
said herbicide being 2,4-D and being characterized by the property of not killing weeds which are grass.

18. The method of claim 11 wherein
said herbicide is glyphosate and is characterized by the property of killing weeds which are grass.

19. The method of claim 1 wherein
said solution has the property of effecting a higher weed kill percentage than either one of said herbicide and said buffer amine oxide applied to said weed alone.

20. The method of claim 1 comprising
said buffered amine oxide containing ethylene glycol, 5Mol borax, boric acid with each present in less than about 1% on a weight basis based on the total solution weight, and
said amine oxide present in a weight percentage based on the entire solution weight of at least about 25% with the balance of said solution being solvent.

21. The method of claim 20 comprising
said amine oxide formula containing about 25 to 35 weight percent of said amine oxide.

22. The method of claim 16 comprising said buffered amine oxide being present in a concentration of about 200:1 to 400:1 on a volume to volume basis.

23. The method of claim 17 comprising said buffered amine oxide being 12 carbon length amine oxide and being selected from the group consisting of (a) potassium phosphate Monobasic/Potassium Phosphate Dibasic, and (b) Potassium Bicarbonate/Potassium Carbonate and Boric Acid/Borax.

24. The method of claim 23 comprising said buffered amine oxide being a mixture of 12 carbon length and 18 carbon length.

25. The method of claim 23 comprising said buffered amine oxide system being 12 carbon length.

26. The method of claim 24 comprising said 12 carbon length on a weight basis being present in an amount of about 1.3 to 2.0 times the amount of 18 carbon length.

27. The method of claim 1 wherein said buffered amine oxide is blended with a combination of amine oxide and a buffer selected from the group consisting (a) Potassium Phosphate Dibasic/ Potassium Phosphate Tribasic, and (b) Potassium Phosphate Monobasic/Potassium Phosphate Dibasic.

28. The method of claim 1 wherein said buffered amine oxide is present in a concentration of about 160:1 to 320:1 on a volume to volume basis.

29. The method of claim 18 wherein said glyphosate is present in said solution in the concentration of about 100:1 to 200:1 on a volume to volume basis.

30. The method of claim 29 comprising said buffered amine oxides selected from the group consisting of
(a) 12 carbon length amine oxides and (b) a mixture of 12 and 18 carbon length amine oxides.

31. The method of claim 2 wherein said buffered amine oxide has a concentration of about 200:1 to 400:1.

32. The method of claim 30 comprising said buffered amine oxide having a 12 carbon length.

33. The method of claim 30 comprising said buffered amine oxide having a mixture of 12 carbon length and 18 carbon length.

34. The method of claim 30 comprising said buffered amine oxide being 12 carbon length amine oxide and said buffer system elected from the group consisting of (a) potassium phosphate Monobasic/Potassium Phosphate Dibasic, and (b) Potassium Bicarbonate/Potassium Carbonate and Boric Acid/Borax.

35. The method of claim 31 wherein said herbicide is present in a concentration of about 50:1 to 200:1 on a volume to volume basis.

36. The method of claim 1 comprising said buffered amine oxide being 12 carbon length amine oxide and said buffer selected from the group consisting of (a) potassium phosphate monobasic/potassium phosphate dibasic and (b) potassium bicarbonate/potassium carbonate.

37. The method of claim 19 comprising said buffered amine oxide having a mixture of 12 carbon length and 18 carbon length and said buffer system selected from the group consisting of (a) potassium phosphate monobasic/potassium phosphate dibasic and (b) potassium bicarbonate/potassium carbonate, and said buffered amine oxide system at the concentration of about 200:1 to 400:1 on a volume to volume basis.

38. The method of claim 7 comprising said buffered amine oxide system being selected from the group consisting of (a) 12 carbon length amine oxide and (b) a mixture of 12 and 18 carbon length amine oxides.

39. The method of claim 38 comprising said buffered amine oxide system having a concentration of about 200:1 to 400:1 on a volume to volume basis.

40. The method of claim 38 comprising said buffered amine oxide system comprising potassium bicarbonate/potassium carbonate.

41. The method of claim 12 comprising said buffered amine oxide being selected from the group consisting of (a) Deprotonated Lycine/Doubly Deprotonated Lycine, (b) Potassium Phosphate Monobasic/Potassium Phosphate Dibasic, and (c) Potassium Bicarbonate/Potassium Cabonate.

42. The method of claim 17 comprising said 2,4-D being present in a concentration of about 200:1 to 400:1.

43. The method of claim 42 comprising said buffered amine oxide having a carbon length selected from the group consisting of (a) a carbon length of 12 and (b) a mixture of carbon lengths 12 and 18.

44. The method of claim 1 comprising said buffered amine oxide being Deprotonated Lysine/Doubly Deprotonated Lysine.

45. The method of claim 12 comprising said buffered amine oxide being Potassium Phosphate Monobasic/Potassium Phosphate Dibasic.

46. The method of claim 42 comprising said buffered amine oxide being Potassium Bicarbonate/Potassium Carbonate.

47. The method of claim 46 comprising said buffered amine oxide having a carbon length of 12.

48. The method of claim 46 comprising said buffered amine oxide having a carbon length which is a mixture of lengths 12 and 18.

49. The method of claim 19 comprising said buffered amine oxide being Ammonium Citrate Tribasic.

50. The method of claim 19 wherein said buffered amine oxide has a concentration of about 200:1 to 400:1 on a volume to volume basis.

51. The method of claim 19 wherein said buffered amine oxide is Potassium Phosphate Monobasic/Potassium Phosphate Dibasic.

52. The method of claim 16 employing said Glyphosate in a concentration of about 100:1 to 200:1 on a volume to volume basis.

53. The method of claim 16 comprising said buffered amine oxide selected from the group consisting of (a) Ammonium/Ammonia (b) Potassium Phosphate Monobasic/Potassium Phosphate Dibasic, and (c) Potassium Bicarbonate/Potassium Carbonate.

54. The method of claim 11 comprising said herbicide being selected from the group consisting of Picloram and Triclopy and combinations thereof.

55. The method of claim 54 comprising said buffered amine oxide having a concentration of about 160:1 to 320:1 on a volume to volume basis.

56. The method of claim 55 comprising said herbicide being present in a range of 100:1 to 200:1 on a volume to volume basis.

57. The method of claim 56 comprising said buffered amine oxide having a concentration of about 200:1 to 400:1 on a volume to volume basis.

58. The method of claim 57 comprising
said buffered amine oxide selected from the group consisting of (a) Deprotonated Lysine/Doubly Deprotonated Lysine, (b) Potassium Phosphate Monobasic/Potassium Phosphate Dibasic, (c) Potassium Bicarbonate/Potassium Carbonate, (d) Boric Acid/Borax and (e) Potassium Phosphate Dibasic/Potassium Phosphate Tribasic.

59. The method of claim 58 comprising
said buffered amine oxide selected from the group consisting of Potassium Phosphate Monobasic/Potassium Phosphate Dibasic and Potassium Bicarbonate/Potassium Carbonate.

60. The method of claim 58 comprising
said buffered amine oxide selected from the group consisting of (a) 12 carbon length amine oxide and (b) a mixture of 12 carbon length amine oxides and 18 carbon length amine oxides.

61. The method of claim 1 wherein
said solution has at least one material selected from the group consisting of insecticides and fungicides, whereby employing a herbicide which does not kill certain plants, will enable insecticides and fungicides to preserve such plants.

62. The method of claim 61 comprising
employing as said herbicide 2,4-D, to kill targeted weeds while assisting with the preservation of plants desired to be preserved.

63. The method of claim 62 comprising
employing said method on grasses which are not killed by said herbicide.

* * * * *

UNITED STATES PATENT AND TRADEMARK OFFICE
CERTIFICATE OF CORRECTION

PATENT NO. : 10,362,783 B2
APPLICATION NO. : 15/238916
DATED : July 30, 2019
INVENTOR(S) : Hans A. Ward et al.

It is certified that error appears in the above-identified patent and that said Letters Patent is hereby corrected as shown below:

In the Specification

Column 1, Line 4, below title, add the following paragraph.
--CROSS-REFERENCE TO RELATED APPLICATION
The present application is a divisional application based on United States Application Serial Number 14/674,498, filed March 31, 2015, now issued United States Patent 10,383,336, which is expressly incorporated herein by reference.--.
Column 4, Line 57, "as a potentially" should read --as potentially--.
Column 5, TABLE 1, Line 12, fourth column, "60"" should read --60--.
Column 5, TABLE 1, Line 15, fifth column, "50"" should read --50--.
Column 5, Line 24, add the following footnotes below TABLE 1.
--*1. Distilled Water Controls*
*2. 20 mature plants*
*3. 10 plots of 90,000 square millimeters of grass plants each*
*4. Mixed types*
*5. 20 milliliters per plant or plot applied with low volume hand applied volumetric sprayer*
*6. Commercial Herbicide mixture concentrate from the time of purchase containing:*
    *4.55% Dimethylamine salt of 2, 4-Dichlorophenoxyacetic acid, and*
    *4.58% Dimethylamine salt of 2-(2-methyl-4-chlorophenoxy) propionic acid, and*
    *4.53% Dimethylamine salt of 2-(2, 4-Dichlorophenoxy) propionic acid*
*7. Commercial Herbicide concentrate from the time of purchase containing:*
    *27% glyphosate isopropylamine salt*
*8. Buffered Amine Oxide Formula: (% wt) 8.67 water, 14.00 ethylene glycol, 8.85 5 Mol Borax, 7.48 Boric Acid, 61.00 Barlox 12 (70% water 30% amine oxide)*
*9. Buffered Amine Oxide formula was added to dilute herbicide solutions, volume to volume.*
*10. No activity of a living plant: dead and decaying--.*
Columns 7-8, Line 24, directly below TABLE 2, add --*See TABLE 1 Footnotes*--.
Column 9, TABLE 3, headings, should read Signed and Sealed this
Twenty-fourth Day of December, 2019

Andrei Iancu
*Director of the United States Patent and Trademark Office*

TABLE 3

| Herbicide Type Product Concentrate Dilution V/V | Component Percent Weight of Buffered Amine Oxide Formula (June 2, 2004)[8] | | | | Weed Type and Kill Rate[10] % 1 Year After Application[5] |
|---|---|---|---|---|---|
| 2, 4-D[6] | Ethylene Glycol | 5 Mol Borax | Boric Acid | Barlox 12 | Raspberry |

Column 9, Line 65, directly below TABLE 3, add --*See TABLE 1 Footnotes*--.
Column 12, Lines 20-31, TABLE 6-continued, should read

TABLE 6–continued

| | Buffer System pH and Total Ion Strengths | | |
|---|---|---|---|
| Buffer No. | Buffer System Name (Abbreviated Name) | pH (Buffer System) | Buffer Total Ion Strength (Molar) |
| 5 | Boric Acid / Borax (Borate Buffer) | 7.7 | 4.95 M |
| A | Potassium Phosphate Dibasic / Potassium Phosphate Tribasic (Phosphate Buffer 2) | 12.1 | 0.500 M |
| B | Potassium Phosphate Monobasic / Potassium Phosphate Dibasic (Phosphate Buffer 3) | 7.5 | 0.500 M |

Column 13, Line 67, "to form a" should be --to form--.
Column 16, Line 58, "Systems A" should read --System A--.
Column 16, Line 59, "systems B" should read --System B--.
Columns 17 and 18, TABLE 8, headings, should read

--TABLE 8

| Herbicide Type Product Concentrate Dilution v/v | No Buffer | September. 2, 2012 to July 4, 2013 Buffered Amine Oxide System Buffer Number & Amine Oxide Donor or Letter[9] | | | | | | | | | | | | Weed Type and Kill Rate[10]% 10 Months After Application[5] |
|---|---|---|---|---|---|---|---|---|---|---|---|---|---|---|
| | | 1 | | 2 | | 3 | | 4 | | 5 | | A | B | |
| Glyphosate[7] | 12 | 1218 | 12 | 1218 | 12 | 1218 | 12 | 1218 | 12 | 1218 | 12 | 1218 | 12 | 1218 | Grasses |

Column 19, Line 60, "Glyphosate 88WSG (a wettable powder)" should read --<u>Glyphosate 88WSG (a wettable powder)</u>--.
Column 19, Line 64, "2,4-D Amine 800WDG" should read --<u>2,4-D Amine 800WDG</u>--.
Column 20, Line 1, "Picloram 20G" should read --<u>Picloram 20G</u>--.
Column 20, Line 6, "Trichloram Brushkiller" should read --<u>Trichloram Brushkiller</u>--.
Column 20, Line 51, "oxide with had" should read --oxide had--.
Column 20, Line 53, "that that using" should read --that using--.
Column 20, Line 65, "shows" should read --show--.
Columns 21-22, TABLE 9 and Columns 23-24, TABLE 9-continued, headings, should read

--TABLE 9

| Herbicide Type Product Concentrate Dilution v/v | No Buffer | February 2013 to November 2013 Buffered Amine Oxide System Buffer Number & Amine Oxide Donor or Letter[8][9] | | | | | | | | | | | | Weed Type and Kill Rate[10]% 240 Days After Application[4] | | |
|---|---|---|---|---|---|---|---|---|---|---|---|---|---|---|---|---|
| | | 1 | | 2 | | 3 | | 4 | | 5 | | 6 | B | | | |
| 2,4-D[6] | 12 | 1218 | 12 | 1218 | 12 | 1218 | 12 | 1218 | 12 | 1218 | 12 | 1218 | 1218 | Broom | Fern | Gorse |

CERTIFICATE OF CORRECTION (continued)
U.S. Pat. No. 10,362,783 B2

Column 24, Line 33, "2-4-d" should read --2,4-D--.
Column 24, Line 34, "no." should read --No.--.
Column 24, Line 58, "200-1" should read --200:1--.
Column 24, Line 59, "400-1" should read --400:1--.
Columns 25-26, TABLE 12, headings, should read

--TABLE 12

| Herbicide Type Product Concentrate Dilution v/v | No Buffer | Buffered Amine Oxide System Buffer Number & Amine Oxide Donor or Letter[8][9] | | | | | | | | | | | | | Weed Type and Kill Rate [10]% 240 Days After Application [4] |
|---|---|---|---|---|---|---|---|---|---|---|---|---|---|---|---|
| | | 1 | | 2 | | 3 | | 4 | | 5 | | 6 | | B | Blackberry |
| 2,4-D[6] | | 12 | 1218 | 12 | 1218 | 12 | 1218 | 12 | 1218 | 12 | 1218 | 12 | 1218 | 1218 | |

--.

Column 25, below TABLE 12, add --*See Table 9 Footnotes*--.
Columns 27-28, TABLE 13, headings, should read

TABLE 13

| Herbicide Type Product Concentrate Dilution v/v | No Buffer | Buffered Amine Oxide System Buffer Number & Amine Oxide Donor or Letter[8][9] | | | | | | | | | | | | | Weed Type and Kill Rate [10]% 240 Days After Application[4] | |
|---|---|---|---|---|---|---|---|---|---|---|---|---|---|---|---|---|
| | | 1 | | 2 | | 3 | | 4 | | 5 | | 6 | | B | Gorse | Blackberry |
| Glyphosphate[7] | | 12 | 1218 | 12 | 1218 | 12 | 1218 | 12 | 1218 | 12 | 1218 | 12 | 1218 | 1218 | | |

--.

Column 27, directly below TABLE 13, add --*See TABLE 9 Footnotes*--.
Columns 29-30, TABLE 14, headings, should read

TABLE 14

| Herbicide Type Product Concentrate Dilution v/v | No Buffer | Buffered Amine Oxide System Buffer Number & Amine Oxide Donor or Letter[8][9] | | | | | | | | | | | | | Weed Type and Kill Rate [10]% 240 Days After Application [4] | | |
|---|---|---|---|---|---|---|---|---|---|---|---|---|---|---|---|---|---|
| | | 1 | | 2 | | 3 | | 4 | | 5 | | 6 | | B | Broom | Fern | Gorse |
| Picloram & Triclopr(5) | | 12 | 1218 | 12 | 1218 | 12 | 1218 | 12 | 1218 | 12 | 1218 | 12 | 1218 | 1218 | | | |

--.

Column 29, Line 58, directly below TABLE 14, add --*See Table 9 Footnotes*--.
Column 30, nineteenth column, TABLE 14, under "Gorse", eighth line, "70" should read --20--.